(12) United States Patent
Renard et al.

(10) Patent No.: US 7,700,303 B2
(45) Date of Patent: Apr. 20, 2010

(54) BIOSENSORS, METHOD FOR OBTAINING THE SAME AND USES THEREOF

(75) Inventors: Martial Renard, Paris (FR); Laurent Belkadi, Montrouge (FR); Patrick England, Paris (FR); Hugues Bedouelle, Paris (FR)

(73) Assignees: Institut Pasteur, Paris (FR); Centre National de la Recherche Scientifique-CNRS, Paris (FR)

( * ) Notice: Subject to any disclaimer, the term of this patent is extended or adjusted under 35 U.S.C. 154(b) by 217 days.

(21) Appl. No.: 11/839,894

(22) Filed: Aug. 16, 2007

(65) Prior Publication Data
US 2009/0017454 A1 Jan. 15, 2009

Related U.S. Application Data

(62) Division of application No. 10/204,431, filed as application No. PCT/FR01/00603 on Mar. 1, 2001, now Pat. No. 7,271,249.

(30) Foreign Application Priority Data
Mar. 1, 2000 (FR) .................................. 00 02657

(51) Int. Cl.
G01N 21/00 (2006.01)
G01N 21/01 (2006.01)
G01N 21/64 (2006.01)
G01N 33/53 (2006.01)
C07K 16/00 (2006.01)
C07K 17/00 (2006.01)
C12P 21/08 (2006.01)

(52) U.S. Cl. ...................... 435/7.1; 435/287.2; 435/328; 422/82.05; 422/82.06; 422/82.07; 422/82.08; 436/164; 436/172; 530/387.1; 530/387.3; 530/391.1

(58) Field of Classification Search .................. None
See application file for complete search history.

(56) References Cited

U.S. PATENT DOCUMENTS

| 5,252,743 | A | 10/1993 | Barrett et al. |
| 5,352,587 | A | 10/1994 | Chang et al. |
| 5,756,351 | A | 5/1998 | Isacoff et al. |
| 5,861,154 | A | 1/1999 | Soda et al. |

FOREIGN PATENT DOCUMENTS

| WO | WO 98/37226 | 8/1998 |
| WO | WO 99/34212 | 7/1999 |

OTHER PUBLICATIONS

Schwartz et al., "A superactive insulin: [B10-aspartic acid]insulin(human)", Proc. Natl. Acad. Sci. USA, 1987, vol. 84, pp. 6408-6411.*
D. Sloan, et al., "Structure-Based Engineering of Environmentally Sensitive Fluorophores For Monitoring Protein-Protein Interactions", Protein Engineering, vol. 11, No. 9, 1998, pp. 819-823. XP-002161420.
R. Narazaki, et al., "Probing The Cysteine 34 Residue In Human Serum Albumin Using Fluorescence Techniques", Biochimica et Biophysica Acta, vol. 1338, No. 2, 1997, pp. 275-281. XP-000987357.
B. Packard, et al., "Site-Directed Labeling of a Monoclonal Antibody: Targeting To a Disulfide Bond", Biochemistry, vol. 25, No. 12, 1986, pp. 3548-3552. XP-002036908.
L. Serrano, et al., "The Folding of an Enzyme II. Substructure of Barnase and the Contribution of Different Interactions to Protein Stability", J. Mol. Biol., vol. 224, No. 3, 1992, pp. 783-804. XP-000989519.
W. Burgess, et al., "Possible Dissociation of the Heparin-Binding and Mitogenic Activities of Heparin-Binding (Acidic Fibroblst) Growth Factor-1 From Its Receptor-Binding Activities By Site-Directed Mutagenesis of a Single Lysine Residue", J. Cell Biol., vol. 111, 1990, pp. 2129-2138.
P. Colman, "Effects of Amino Acid Sequence Changes on Antibody-antigen Interactons", Research in Immunology, vol. 145, 1994, pp. 33-36.
U. Gether, et al., "Fluorescent Labeling of Purified $\beta_2$ Adrenergic Receptor", The Journal of Biological Chemistry, vol. 270, No. 47, 1995, pp. 28268-28275.
G. Ibragimova, et al., "Stability of the β-Sheet of the WW Domain: A Molecular Dynamics Simulation Study", Biophysical Journal, vol. 77, No. 4, 1999, pp. 2191-2198.
E. Lazar, et al., "Transforming Growth Factor α: Mutation of Aspartic Acid 47 Leucine 48 Results in Different Biological Activities", Molecular and Cellular Biology, vol. 8, No. 3, 1988, pp. 1247-1252.
M. Lin, et al., "Structure-Function Relationships I Glucagon: Properties of Highly Purfied Des-His$^1$-, Monoiodo-, and [Des-Asn$^{28}$, Thr$^{29}$](homoserine lactone$^{27}$)-glucagon", Biochemistry, vol. 14, No. 8, 1975, pp. 1559-1563.
S. Rudikoff, et al., "Single Amino Acid Substitution Altering Antigen-Binding Specificity", Proc. Nat'l. Acad. Sci. USA, vol. 79, No. 6, 1982, pp. 1979-1983.
G. Schwartz, et al., "A Superactive Insulin: [B 10-aspartic Acid]Insulin(Human)",Proc. Nat'l, Acad. Sci. USA, vol. 84, No. 1, 1987, pp. 6408-6411.
C. Bandtlow, et al., "The *Escherichia coli*-Derived Fab fragment of the IgM/k Antibody IN-1 Recognizes and Neutralizes Myelin-Associated Inhibitors of Neurite Growth", Eur. J. Biochem., vol. 241, No. 2, 1996, pp. 468-475. XP-000991434.
J. Wu, et al., "Cysteine 148 In The Lactose Permease of *Escherichia coli* Is A Component of A Substrate Binding Site. 2. Site-Directed Fluorescence Studies", Biochemistry, vol. 33, No. 40, 1994, pp. 12166-12171. XP-002172185.

(Continued)

*Primary Examiner*—Unsu Jung
(74) *Attorney, Agent, or Firm*—Oblon, Spivak, McClelland, Maier & Neustadt, L.L.P.

(57) ABSTRACT

The invention relates to biosensors, methods for obtaining them and their use for detecting, assaying or locating, in direct immunofluorescence, a ligand such as an antigen or hapten, in a heterogeneous population. The biosensor includes (i) at least one fragment of a receptor which is protein in nature, capable of binding to a ligand via an active site, where at least one amino acid residues of the fragment located in the proximity of the active site is naturally present in the form of a cystein (Cys) residue, or is substituted with a Cys residue, and (ii) a fluorophore coupled to the Cys residue.

16 Claims, 13 Drawing Sheets

OTHER PUBLICATIONS

S. Pollack, et al., "Introduction of Nucleophiles and Spectroscopic Probes into Antibody Combining Sites", Science, vol. 242, No. 4881, 1988, pp. 1038-1040, XP-000996977.

P. Acland, et al., "Subcellular Fate of the Int-2 Oncoprotein is Determined By Choice of Initiation Condo", Nature, vol. 343, No. 6259, 1990, pp. 662-665.

* cited by examiner

FIG. 1

| Residue | Proximity (Å) | ASA in free FV (%) | | | | ASA in Fv::HEL (%) | | | | Mutation | ΔΔG kcal/mol | Choice |
|---|---|---|---|---|---|---|---|---|---|---|---|---|
| | | Xγ | Xδ | Xγ | Xε | Xγ | Xδ | Xγ | Xε | | | |
| VL-Asn28 | 2.0 | 7.4 | 2.3, 59.8 | 7.8 | | | 2.5, 59.9 | | | A | 0.8 | ? |
| VL-His30 | d | 0.0 | 81.4, 0.0 | 0.0 | | | 17.4, 0.0 | 41.3, 36.2 | | A | | ? |
| VL-Asn31 | 2.0 | 54.8 | 39.3, 35.6 | 54.5 | | | 39.2, 35.6 | | | A, F | 1.7, 2.0 | # |
| VL-Tyr32 | d | 0.0 | 5.4, 0.0 | 0.0 | | | 5.3, 0.0 | 2.9, 11.0 | | A | 0.8 | - |
| VL-Tyr49 | d | 0.0 | 0.0, 17.5 | 0.0 | | | 0.0, 16.0 | 22.0, 0.0 | | A, F, N | 0.5, 0.5, 2.3 | - |
| VL-Tyr50 | d | 100 | 17.7, 83.0 | 53.3 | | | 10.2, 14.2 | 0.0, 27.7 | | K | 0 | # |
| VL-Thr52 | 1.4 | 67.6, 46.2 | | 65.0, 46.2 | | | | | | A | <0.5 | + |
| VL-Thr53 | d | 50.6, 53.8 | | 12.7, 44.4 | | | | | | | | # |
| VL-Asp56 | 2.6 | 100 | | 100 | | | | | | | | |
| VL-Gly68 | 2.9 | | | | | 99.6, 98.8 | | | | | | - |
| VL-Phe91 | d (b) | 0.0 | 0.0, 0.0 | 0.0 | | | 0.0, 0.0 | 0.0, 0.0 | | A | 3.7 | + |
| VL-Trp92 | d | 0.0 | 14.5, 0.0 | 0.0 | | | 14.6, 0.0 | 68.3, 0.0, 0.0 | | A | 0.3 | + |
| VL-Ser93 | d | 89.7 | | 56.0 | | | | | | | | |
| VL-Thr94 | i, 1.7 | 54.5, 7.2 | | 54.5, 51.7 | | 7.2 | | | | | | |
| VH-Phe27 | 2.9 | 0.0 | 0.0, 0.0 | 0.0 | | | 0.0, 0.0 | 0.0, 0.0 | | N(+E46Q) | 1.1 | - |
| VH-Ser28 | 2.0 | 45.0 | | 44.8 | | | | | | | | # |
| VH-Thr30 | i, 1.4 | 62.6, 51.7 | | 62.5, 51.7 | | | | | | A | 0.1 | + |
| VH-Gly31 | d | | | | | | | | | | | |
| VH-Tyr32 | 1.4 | 0.0 | 0.0, 5.3 | 0.0 | | | 0.0, 5.3 | 18.7, 4.9 | | A, F | 1.1, 0.4 | - |
| VH-Gly33 | d | | | | | | | | | | | |
| VH-Trp52 | d | 65.6 | 6.4, 59.5 | 40.0 | | | 6.4, 0.0 | 8.1, 0.0, 8.6 | | A | 0.9 | - |
| VH-Gly53 | d | | | | | | | | | | | |
| VH-Asp54 | d | 24.3 | 0.0, 83.8 | 5.7 | | | 0.0, 36.7 | | | A | 1.9 | # |
| VH-Asn56 | 2.3 | 89.7 | 46.9, 100 | 89.2 | | | 47.0, 100 | | | A, S | 0.2, 0.2 | ? |
| VH-Asp58 | 1.7 | 14.4 | 79.3, 26.0 | 14.3 | | | 79.2, 26.1 | | | A | 0 | . |
| VH-Arg97 | 2.3 | 0.0 | 0.0 | 0.0 | | | 0.0 | 0.0 | | A | 0.1 | . |
| VH-Arg99 | d | 23.0 | 1.7 | 23.2 | | | 1.8 | 44.8 | | A, N | 3.1, 3.7 | ? |
| VH-Asp100 | d | 96.9 | | 6.5 | | | 2.8 | 1.2 | | A, F | >4, 2.5 | . |
| VH-Tyr101 | d | 0.0 | 54.5, 72.4 | 0.0 | | | 0.0, 0.0 | 4.2, 7.9 | | | 1.6, 3.2 | . |
| VH-Arg102 | d | 0.8 | 0.0, 12.7 | 0.9 | | | 1.5 | 18.6 | | K, M | | - |

CNBD

IANBD

5-IAF

Acrylodan

| β-mercaptoethanol | Mutant | Coupling yield | Material yield |
|---|---|---|---|
| 50 mM | VH-T30C | not measurable | 5 % |
| 10 mM | VH-T30C | 72 % | 19 % |
| 50 mM | VL-S93C | > 168 % | 4 % |
| 10 mM | VL-S93C | 83 % | 9 % |
| 1 mM | VL-S93C | 34 % | 12 % |
| 1 mM | VL-S93C | 34 % | 12 % |
| no reduction | VL-S93C | 8 % | 85 % |

FIGURE 9

| Position | Coupling yield (%) | Variation in Fluorescence (%) |
|---|---|---|
| wt | < 8% | |
| VL-His30 | 116% | + 7 % |
| VL-Asn31 | 103% | + 16 % |
| VL-Tyr49 | 78% | + 75 % |
| VL-Tyr50 | 88% | + 1 % |
| VL-Thr52 | 83% | + 12 % |
| VL-Thr53 | 104% | + 13 % |
| VL-Asp56 | 116% | - 1 % |
| VL-Trp92 | 107% | + 53 % |
| VL-Ser93 | 83% | + 26 % |
| VL-Thr94 | 94% | + 55 % |
| VH-Ser28 | 111% | - 2 % |
| VH-Thr30 | 72% | - 6 % |
| VH-Gly31 | 130% | - 2 % |
| VH-Tyr32 | 85% | + 26 % |
| VH-Gly53 | 42% | + 1 % |
| VH-Asn56 | 92% | + 5 % |
| VH-Arg99 | 101% | - 6 % |

FIGURE 13

SEQUENCE LISTING

```
<160> NUMBER OF SEQ ID NOS: 25

<210> SEQ ID NO 1
<211> LENGTH: 27
<212> TYPE: DNA
<213> ORGANISM: ARTIFICIAL SEQUENCE
<220> FEATURE:
<223> OTHER INFORMATION: SYNTHETIC DNA

<400> SEQUENCE: 1
catctgctaa gcatgttgta taataga                                       27

<210> SEQ ID NO 2
<211> LENGTH: 29
<212> TYPE: DNA
<213> ORGANISM: ARTIFICIAL SEQUENCE
<220> FEATURE:
<223> OTHER INFORMATION: SYNTHETIC DNA

<400> SEQUENCE: 2
cgaggagtac accaaaaatg ttgacagta                                     29

<210> SEQ ID NO 3
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 3
cgtccgagga caactccaaa aatgtt                                        26

<210> SEQ ID NO 4
<211> LENGTH: 18
<212> TYPE: DNA
<213> ORGANISM: ARTIFICIAL SEQUENCE
<220> FEATURE:
<223> OTHER INFORMATION: SYNTHETIC DNA

<400> SEQUENCE: 4
agaatattgt gttcctga                                                 18

<210> SEQ ID NO 5
<211> LENGTH: 18
<212> TYPE: DNA
<213> ORGANISM: ARTIFICIAL SEQUENCE
<220> FEATURE:
<223> OTHER INFORMATION: SYNTHETIC DNA
```

-continued

```
<400> SEQUENCE: 5
tgctgatgct cagtctgg                                                    18

<210> SEQ ID NO 6
<211> LENGTH: 18
<212> TYPE: DNA
<213> ORGANISM: ARTIFICIAL SEQUENCE
<220> FEATURE:
<223> OTHER INFORMATION: SYNTHETIC DNA

<400> SEQUENCE: 6
ggtgatggaa acacagac                                                    18

<210> SEQ ID NO 7
<211> LENGTH: 15
<212> TYPE: DNA
<213> ORGANISM: ARTIFICIAL SEQUENCE
<220> FEATURE:
<223> OTHER INFORMATION: SYNTHETIC DNA

<400> SEQUENCE: 7
cgccgcgctt aatgc                                                       15

<210> SEQ ID NO 8
<211> LENGTH: 43
<212> TYPE: DNA
<213> ORGANISM: ARTIFICIAL SEQUENCE
<220> FEATURE:
<223> OTHER INFORMATION: SYNTHETIC DNA

<400> SEQUENCE: 8
tcgagatcaa gcggccgctg gaacaccatc accatcacca tta                        43

<210> SEQ ID NO 9
<211> LENGTH: 43
<212> TYPE: DNA
<213> ORGANISM: ARTIFICIAL SEQUENCE
<220> FEATURE:
<223> OTHER INFORMATION: SYNTHETIC DNA

<400> SEQUENCE: 9
agcttaatgg tgatggtgat ggtggtccag cggccgcttg atc                        43

<210> SEQ ID NO 10
<211> LENGTH: 3922
<212> TYPE: DNA
<213> ORGANISM: ARTIFICIAL SEQUENCE
<220> FEATURE:
<223> OTHER INFORMATION: SYNTHETIC DNA

<400> SEQUENCE: 10
acccgacacc atcgaatggc cagatgatta attcctaatt tttgttgaca ctctatcatt      60
gatagagtta ttttaccact ccctatcagt gatagagaaa agtgaaatga atagttcgac     120
aaaaatctag ataacgaggg caaaaaatga aaagacagc tatcgcgatt gcagtggcac      180
tggctggttt cgctaccgta gcgcaggccg aagttaaact gcaggagtca ggacctggcc    240
tggtggcgcc ctcacagagc ctgtccatca catgcaccgt ctcagggttc tcattaaccg    300
gctatggtgt aaactgggtt cgccagcctc caggaaaggg tctggagtgg ctggaatga    360 tttggggtga tggaaacaca gactataatt cagctctcaa atccagactg agcatcagca    420
aggacaactc caagagccaa gttttcttaa aaatgaacag tctgcacact gatgacacag    480
ccaggtacta ctgtgccaga gagagagatt ataggcttga ctactggggc caagggacca    540
```

-continued

```
cggtcaccgt ctcctcaggt ggaggcggtt caggcggagg tggctctggc ggtggcggat      600
cggacatcga gctcacccag tctccagcct ccctttctgc gtctgtggga gaaactgtca      660
ccatcacatg tcgagcaagt gggaatattc acaattattt agcatggtat cagcagaaac      720
agggaaaatc tcctcagctc ctggtctatt atacaacaac cttagcagat ggtgtgccat      780
caaggttcag tggcagtgga tcaggaacac aatattctct caagatcaac agcctgcaac      840
ctgaagattt tgggagttat tactgtcaac attttggag tactcctcgg acgttcggtg       900
gagggaccaa gctcgagatc aagcggccgc tggaacacca tcaccatcac cattaagctt      960
gacctgtgaa gtgaaaatg gcgcacattg tgcgacattt ttttgtctg ccgtttaccg       1020 ctactgcgtc acggatctcc acgcgccctg tagcggcgca ttaagcgcgg cgggtgtggt     1080
ggttacgcgc agcgtgaccg ctacacttgc cagcgcccta gcgcccgctc ctttcgcttt     1140
cttcccttcc tttctcgcca cgttcgccgg ctttccccgt caagctctaa atcgggggct     1200 cccctttaggg ttccgattta gtgctttacg gcacctcgac cccaaaaaac ttgattaggg   1260
tgatggttca cgtagtgggc catcgccctg atagacggtt tttcgccctt tgacgttgga     1320
gtccacgttc tttaatagtg gactcttgtt ccaaactgga caacactca accctatctc     1380 ggtctattct tttgatttat aagggatttt gccgatttcg gcctattggt taaaaaatga     1440
gctgatttaa caaaaattta acgcgaattt taacaaaata ttaacgctta caatttcagg    1500
tggcactttt cggggaaatg tgcgcggaac ccctatttgt ttattttct aaatacattc     1560 aaatatgtat ccgctcatga acaataacc ctgataaatg cttcaataat attgaaaaag     1620
gaagagtatg agtattcaac atttccgtgt cgcccttatt cccttttttg cggcattttg     1680
ccttcctgtt tttgctcacc cagaaacgct ggtgaaagta aaagatgctg aagatcagtt     1740
gggtgcacga gtgggttaca tcgaactgga tctcaacagc ggtaagatcc ttgagagttt     1800
tcgccccgaa gaacgttttc caatgatgag cacttttaaa gttctgctat gtggcgcggt     1860
attatcccgt attgacgccg ggcaagagca actcggtcgc cgcatacact attctcagaa     1920
tgacttggtt gagtactcac cagtcacaga aaagcatctt acggatggca tgacagtaag     1980
agaattatgc agtgctgcca taaccatgag tgataacact gcggccaact tacttctgac     2040
aacgatcgga ggaccgaagg agctaaccgc ttttttgcac aacatggggg atcatgtaac     2100
tcgccttgat cgttgggaac cggagctgaa tgaagccata ccaaacgacg agcgtgacac     2160
cacgatgcct gtagcaatgg caacaacgtt gcgcaaacta ttaactggcg aactacttac     2220
tctagcttcc cggcaacaat tgatagactg gatggaggcg gataaagttg caggaccact     2280
tctgcgctcg gcccttccgg ctggctggtt tattgctgat aaatctggag ccggtgagcg     2340
tggctctcgc ggtatcattg cagcactggg gccagatggt aagccctccc gtatcgtagt     2400
tatctacacg acggggagtc aggcaactat ggatgaacga atagacaga tcgctgagat     2460 aggtgcctca ctgattaagc attggtagga attaatgatg tctcgtttag ataaaagtaa    2520
agtgattaac agcgcattag agctgcttaa tgaggtcgga atcgaaggtt taacaacccg     2580
taaactcgcc cagaagctag gtgtagagca gcctacattg tattggcatg taaaaaataa    2640
gcgggctttg ctcgacgcct tagccattga gatgttagat aggcaccata ctcacttttg    2700
ccctttagaa ggggaaagct ggcaagattt tttacgtaat aacgctaaaa gttttagatg    2760
tgctttacta agtcatcgcg atggagcaaa agtacattta ggtacacggc ctacagaaaa    2820
acagtatgaa actctcgaaa atcaattagc ctttttatgc caacaaggtt tttcactaga    2880
```

-continued

| | | |
|---|---|---|
| gaatgcatta tatgcactca gcgcagtggg gcattttact ttaggttgcg tattggaaga | 2940 |
| tcaagagcat caagtcgcta agaagaaag ggaaacacct actactgata gtatgccgcc | 3000 |
| attattacga caagctatcg aattatttga tcaccaaggt gcagagccag ccttcttatt | 3060 |
| cggccttgaa ttgatcatat gcggattaga aaaacaactt aaatgtgaaa gtgggtctta | 3120 |
| aaagcagcat aaccttttc cgtgatggta acttcactag tttaaaagga tctaggtgaa | 3180 |
| gatccttttt gataatctca tgaccaaaat cccttaacgt gagttttcgt tccactgagc | 3240 |
| gtcagacccc gtagaaaaga tcaaaggatc ttcttgagat cctttttttc tgcgcgtaat | 3300 |
| ctgctgcttg caaacaaaaa aaccaccgct accagcggtg gtttgtttgc cggatcaaga | 3360 |
| gctaccaact ctttttccga aggtaactgg cttcagcaga gcgcagatac caaatactgt | 3420 |
| ccttctagtg tagccgtagt taggccacca cttcaagaac tctgtagcac cgcctacata | 3480 |
| cctcgctctg ctaatcctgt taccagtggc tgctgccagt ggcgataagt cgtgtcttac | 3540 |
| cgggttggac tcaagacgat agttaccgga taaggcgcag cggtcgggct gaacggggggg | 3600 |
| ttcgtgcaca cagcccagct tggagcgaac gacctacacc gaactgagat acctacagcg | 3660 |
| tgagctatga gaaagcgcca cgcttcccga agggagaaag gcggacaggt atccggtaag | 3720 |
| cggcagggtc ggaacaggag agcgcacgag ggagcttcca gggggaaacg cctggtatct | 3780 |
| ttatagtcct gtcgggtttc gccacctctg acttgagcgt cgattttgt gatgctcgtc | 3840 |
| agggggggcgg agcctatgga aaaacgccag caacgcggcc tttttacggt tcctggcctt | 3900 |
| ttgctggcct tttgctcaca tg | 3922 |

<210> SEQ ID NO 11
<211> LENGTH: 3922
<212> TYPE: DNA
<213> ORGANISM: ARTIFICIAL SEQUENCE
<220> FEATURE:
<223> OTHER INFORMATION: SYNTHETIC DNA

<400> SEQUENCE: 11

| | | |
|---|---|---|
| acccgacacc atcgaatggc cagatgatta attcctaatt tttgttgaca ctctatcatt | 60 |
| gatagagtta ttttaccact ccctatcagt gatagagaaa agtgaaatga atagttcgac | 120 |
| aaaaatctag ataacgaggg caaaaaatga aaaagacagc tatcgcgatt gcagtggcac | 180 |
| tggctggttt cgctaccgta gcgcaggccg aagttaaact gcaggagtca ggacctggcc | 240 |
| tggtggcgcc ctcacagagc ctgtccatca catgcaccgt ctcagggttc tcattaaccg | 300 |
| gctatggtgt aaactgggtt cgccagcctc caggaaaggg tctggagtgg ctgggaatga | 360 |
| tttggggtga tggaaacaca gactataatt cagctctcaa atccagactg agcatcagca | 420 |
| aggacaactc caagagccaa gttttcttaa aaatgaacag tctgcacact gatgacacag | 480 |
| ccaggtacta ctgtgccaga gagagagatt ataggcttga ctactggggc caagggacca | 540 |
| cggtcaccgt ctcctcaggt ggaggcggtt caggcggagg tggctctggc ggtggcggat | 600 |
| cggacatcga gctcacccag tctccagcct cccttctgc gtctgtggga gaaactgtca | 660 |
| ccatcacatg tcgagcaagt gggaatattc acaattattt agcatggtat cagcagaaac | 720 |
| agggaaaatc tcctcagctc ctggtctatt atacaacaac cttagcagat ggtgtgccat | 780 |
| caaggttcag tggcagtgga tcaggaacac aatattctct caagatcaac agcctgcaac | 840 |
| ctgaagattt tgggagttat tactgtcaac attttggtg tactcctcgg acgttcggtg | 900 |
| gagggaccaa gctcgagatc aagcggccgc tggaacacca tcaccatcac cattaagctt | 960 |
| gacctgtgaa gtgaaaaatg gcgcacattg tgcgacattt ttttgtctg ccgtttaccg | 1020 |

-continued

```
ctactgcgtc acggatctcc acgcgccctg tagcggcgca ttaagcgcgg cgggtgtggt      1080
ggttacgcgc agcgtgaccg ctacacttgc cagcgcccta gcgcccgctc ctttcgcttt      1140
cttcccttcc tttctcgcca cgttcgccgg ctttccccgt caagctctaa atcgggggct      1200
cccctttaggg ttccgattta gtgctttacg gcacctcgac cccaaaaaac ttgattaggg     1260
tgatggttca cgtagtgggc catcgccctg atagacggtt tttcgccctt tgacgttgga      1320
gtccacgttc tttaatagtg gactcttgtt ccaaactgga acaacactca accctatctc      1380
ggtctattct tttgatttat aagggatttt gccgatttcg gcctattggt taaaaaatga      1440
gctgatttaa caaaaattta acgcgaattt taacaaaata ttaacgctta caatttcagg      1500
tggcactttt cggggaaatg tgcgcggaac ccctatttgt ttatttttct aaatacattc      1560
aaatatgtat ccgctcatga acaataacc ctgataaatg cttcaataat attgaaaaag       1620
gaagagtatg agtattcaac atttccgtgt cgcccttatt ccctttttg cggcatttg        1680
ccttcctgtt tttgctcacc cagaaacgct ggtgaaagta aaagatgctg aagatcagtt      1740
gggtgcacga gtgggttaca tcgaactgga tctcaacagc ggtaagatcc ttgagagttt      1800
tcgccccgaa gaacgttttc caatgatgag cacttttaaa gttctgctat gtggcgcggt      1860
attatcccgt attgacgccg ggcaagagca actcggtcgc cgcatacact attctcagaa      1920
tgacttggtt gagtactcac cagtcacaga aaagcatctt acggatggca tgacagtaag      1980
agaattatgc agtgctgcca taaccatgag tgataacact gcggccaact tacttctgac      2040
aacgatcgga ggaccgaagg agctaaccgc ttttttgcac aacatggggg atcatgtaac      2100
tcgccttgat cgttgggaac cggagctgaa tgaagccata ccaaacgacg agcgtgacac      2160
cacgatgcct gtagcaatgg caacaacgtt gcgcaaacta ttaactggcg aactacttac      2220
tctagcttcc cggcaacaat tgatagactg gatggaggcg gataaagttg caggaccact      2280
tctgcgctcg gcccttccgg ctggctggtt tattgctgat aaatctggag ccggtgagcg      2340
tggctctcgc ggtatcattg cagcactggg gccagatggt aagccctccc gtatcgtagt      2400
tatctacacg acggggagtc aggcaactat ggatgaacga atatagacaga tcgctgagat     2460
aggtgcctca ctgattaagc attggtagga attaatgatg tctcgtttag ataaaagtaa      2520
agtgattaac agcgcattag agctgcttaa tgaggtcgga atcgaaggtt taacaacccg      2580
taaactcgcc cagaagctag gtgtagagca gcctacattg tattggcatg taaaaaataa      2640
gcgggctttg ctcgacgcct tagccattga gatgttagat aggcaccata ctcacttttg      2700
ccctttagaa ggggaaagct ggcaagattt tttacgtaat aacgctaaaa gttttagatg      2760
tgctttacta agtcatcgcg atggagcaaa agtacattta ggtacacggc ctacagaaaa      2820
acagtatgaa actctcgaaa atcaattagc cttttatgc caacaaggtt tttcactaga       2880
gaatgcatta tatgcactca gcgcagtggg gcatttact ttaggttgcg tattggaaga       2940
tcaagagcat caagtcgcta aagaagaaag ggaaacacct actactgata gtatgccgcc      3000
attattacga caagctatcg aattatttga tcaccaaggt gcagagccag ccttcttatt      3060
cggccttgaa ttgatcatat gcggattaga aaaacaactt aaatgtgaaa gtgggtctta      3120
aaagcagcat aaccttttc cgtgatggta acttcactag tttaaaagga tctaggtgaa       3180
gatcctttt gataatctca tgaccaaaat cccttaacgt gagttttcgt tccactgagc       3240
gtcagacccc gtagaaaaga tcaaaggatc ttcttgagat cctttttttc tgcgcgtaat      3300
ctgctgcttg caaacaaaaa aaccaccgct accagcggtg gtttgtttgc cggatcaaga      3360
```

-continued

```
gctaccaact cttttttccga aggtaactgg cttcagcaga gcgcagatac caaatactgt    3420
ccttctagtg tagccgtagt taggccacca cttcaagaac tctgtagcac cgcctacata    3480
cctcgctctg ctaatcctgt taccagtggc tgctgccagt ggcgataagt cgtgtcttac    3540
cgggttggac tcaagacgat agttaccgga taaggcgcag cggtcgggct gaacgggggg    3600
ttcgtgcaca cagcccagct tggagcgaac gacctacacc gaactgagat acctacagcg    3660
tgagctatga gaaagcgcca cgcttcccga agggagaaag gcggacaggt atccggtaag    3720
cggcagggtc ggaacaggag agcgcacgag ggagcttcca gggggaaacg cctggtatct    3780
ttatagtcct gtcgggtttc gccacctctg acttgagcgt cgatttttgt gatgctcgtc    3840 agggggggcgg agcctatgga aaaacgccag caacgcggcc ttttttacggt tcctggcctt    3900 ttgctggcct tttgctcaca tg                                              3922
```

<210> SEQ ID NO 12
<211> LENGTH: 28
<212> TYPE: DNA
<213> ORGANISM: ARTIFICIAL SEQUENCE
<220> FEATURE:
<223> OTHER INFORMATION: SYNTHETIC DNA

<400> SEQUENCE: 12

```
gaggagtacg caaaaatgtt gacagtaa                                          28
```

<210> SEQ ID NO 13
<211> LENGTH: 28
<212> TYPE: DNA
<213> ORGANISM: ARTIFICIAL SEQUENCE
<220> FEATURE:
<223> OTHER INFORMATION: SYNTHETIC DNA

<400> SEQUENCE: 13

```
catctgctaa ggtacatgta taatagac                                          28
```

<210> SEQ ID NO 14
<211> LENGTH: 28
<212> TYPE: DNA
<213> ORGANISM: ARTIFICIAL SEQUENCE
<220> FEATURE:
<223> OTHER INFORMATION: SYNTHETIC DNA

<400> SEQUENCE: 14

```
cagtttacac cacacccggt taatgaga                                          28
```

<210> SEQ ID NO 15
<211> LENGTH: 28
<212> TYPE: DNA
<213> ORGANISM: ARTIFICIAL SEQUENCE
<220> FEATURE:
<223> OTHER INFORMATION: SYNTHETIC DNA

<400> SEQUENCE: 15

```
acaccatagc cgcataatga gaaccctg                                          28
```

<210> SEQ ID NO 16
<211> LENGTH: 31
<212> TYPE: DNA
<213> ORGANISM: ARTIFICIAL SEQUENCE
<220> FEATURE:
<223> OTHER INFORMATION: SYNTHETIC DNA

<400> SEQUENCE: 16

```
cttgatggca caccgcatgc taaggttgtt g                                      31
```

<210> SEQ ID NO 17
<211> LENGTH: 31
<212> TYPE: DNA
<213> ORGANISM: ARTIFICIAL SEQUENCE
<220> FEATURE:
<223> OTHER INFORMATION: SYNTHETIC DNA

<400> SEQUENCE: 17
catgctaaat aacagtggat attcccactt g                                31

<210> SEQ ID NO 18
<211> LENGTH: 33
<212> TYPE: DNA
<213> ORGANISM: ARTIFICIAL SEQUENCE
<220> FEATURE:
<223> OTHER INFORMATION: SYNTHETIC DNA

<400> SEQUENCE: 18
acaccatagc cagttaagca gaaccctgag acg                              33

<210> SEQ ID NO 19
<211> LENGTH: 32
<212> TYPE: DNA
<213> ORGANISM: ARTIFICIAL SEQUENCE
<220> FEATURE:
<223> OTHER INFORMATION: SYNTHETIC DNA

<400> SEQUENCE: 19
ttatagtctg tgcacccatc accccaaatc at                               32

<210> SEQ ID NO 20
<211> LENGTH: 31
<212> TYPE: DNA
<213> ORGANISM: ARTIFICIAL SEQUENCE
<220> FEATURE:
<223> OTHER INFORMATION: SYNTHETIC DNA

<400> SEQUENCE: 20
atggtacgat ttattaaaca ttataagggt g                                31

<210> SEQ ID NO 21
<211> LENGTH: 34
<212> TYPE: DNA
<213> ORGANISM: ARTIFICIAL SEQUENCE
<220> FEATURE:
<223> OTHER INFORMATION: SYNTHETIC DNA

<400> SEQUENCE: 21
agacgattcc aacaacatat acactggtcc tcga                             34

<210> SEQ ID NO 22
<211> LENGTH: 35
<212> TYPE: DNA
<213> ORGANISM: ARTIFICIAL SEQUENCE
<220> FEATURE:
<223> OTHER INFORMATION: SYNTHETIC DNA

<400> SEQUENCE: 22
gattccaaca acatatctgg tcctcgactc ctcta                            35

<210> SEQ ID NO 23
<211> LENGTH: 36
<212> TYPE: DNA
<213> ORGANISM: ARTIFICIAL SEQUENCE
<220> FEATURE:

-continued

```
<223> OTHER INFORMATION: SYNTHETIC DNA

<400> SEQUENCE: 23
tgacacggtc tctcacacta atatccgaac tgatga                              36

<210> SEQ ID NO 24
<211> LENGTH: 28
<212> TYPE: DNA
<213> ORGANISM: ARTIFICIAL SEQUENCE
<220> FEATURE:
<223> OTHER INFORMATION: SYNTHETIC DNA

<400> SEQUENCE: 24
caagagtaat tggacaatac cacatttg                                       28

<210> SEQ ID NO 25
<211> LENGTH: 32
<212> TYPE: DNA
<213> ORGANISM: ARTIFICIAL SEQUENCE
<220> FEATURE:
<223> OTHER INFORMATION: SYNTHETIC DNA

<400> SEQUENCE: 25
acccttacta aacacaacta cctttgtgtc tg                                  32
```

BIOSENSORS, METHOD FOR OBTAINING THE SAME AND USES THEREOF

This application is a Divisional of U.S. application Ser. No. 10/204,431, filed on Aug. 30, 2002, allowed, which is the National Stage of PCT/FR01/00603, filed Mar. 1, 2001.

The present invention relates to biosensors, to the method for obtaining the same and to uses thereof, in particular for detecting, assaying or locating, by direct immunofluorescence, a ligand such as an antigen or a hapten, in a heterogeneous population.

A biosensor is a bifunctional biological macromolecule: firstly, it is capable of specifically binding its ligand in a mixture; secondly, it translates the binding event into a signal which can be measured directly and instantaneously: by means of a simple system of diodes, of a spectrofluorimeter, of a fluorescence microscope, of a confocal microscope, or of any other device, the consequence of which being that the detection thus carried out is immediate.

Although DNA "chips" for detecting nucleic acid sequences already exist, a general solution for constructing biosensors and chips based on proteins, allowing the detection of other ligands, does not exist and therefore remains to be developed.

Several approaches to this have been tried:

in the case of proteins which do not have cysteine (Cys) residues or, a fortiori, disulfide bridges, a cysteine has been introduced into the protein by site-directed mutagenesis. The cysteine is introduced either in the immediate proximity of the ligand-binding site (protein GB1; Sloan et al., 1998) or at a distance from this site (MBP protein; Gilardi et al., 1994; Marvin et al., 1997; GBP protein; Marvin et al., 1998; Tolosa et al., 1999). The thiol function thus added allows coupling to a fluorophore sensitive to its electron environment. The binding of the ligand then modifies this environment and the change in the properties of the biosensor is thus directly detectable by spectrofluorimetry. For example, Sloan et al. (1998) have in particular shown that the fluorophore should be positioned in a region located at the protein-protein interface, and they have studied the coupling of a fluorophore in a region of this type, for the GB1 domain-Fc complex: in this context, the formation of the complex is analyzed; the best results are obtained when the fluorophore is coupled at an amino acid involved in the formation of the complex.

However, this approach concerns only very particular proteins which have no free cysteine residue and no cysteine residues involved in disulfide bridges. Moreover, the use of the abovementioned biosensors is limited to the detection of a few particular ligands (maltose, glucose and antibody Fc fragment). In fact, in this approach, the main difficulty in creating biosensors, using a protein which contains disulfide bridges, comes from the fact that the steps for coupling the fluorophore to a Cys residue may result in disulfide bridges, which are essential for the structure and stability, being attacked and the molecule being inactivated. Among these proteins, antibodies represent the class of proteins naturally dedicated to the specific binding of protein, peptide, polysaccharide or hapten ligands (antigens) with great affinity. However, antibody molecules have Cys residues which form intra- and interchain disulfide bridges. In particular, the Fv fragments of antibodies comprise two disulfide bridges, one in each of the VH and VL domains, which are essential for the stability of the Fv fragment or of single-chain fragments, scFv (Glockshuber et al., 1992).

a biosensor has been derived from an antibody which binds 2,4-dinitrophenol, using the following approach. A thiol group was introduced in the proximity of the ligand-binding site using an affinity label which combined, in the same molecule, a 2,4-dinitrophenol group recognized specifically by the antibody, a thiophenyl or disulfide linkage, and an aldehyde or alpha-bromoketone reactive group. The affinity label was capable of binding to the binding site of the antibody via the 2,4-dinitrophenol group, and then of coupling to the antibody by random reaction of its aldehyde or alpha-bromoketone group with the side chains of the Lys, His or Tyr residues located nearby. Treatment of the coupled antibody with dithiothreitol liberated an SH group which could, in turn, be coupled to a fluorophore (Pollack et al., 1988).

This method has the drawback that it is random, cannot be generalized, and applies only to antibodies directed against haptens since it depends on the existence of Lys, His or Tyr residues at a correct distance from the binding site of the antibody and on the possibility of synthesizing a three-part affinity label as described above.

The inventors have given themselves the aim of enabling protein-based biosensors to be obtained using a rational, general and generalizable method capable of identifying the amino acid residues of a protein receptor which may be substituted with cysteine residues. Such biosensors correspond better to practical needs, in particular in that they allow coupling of a fluorophore at a position which induces a change in the structural environment of the fluorophore during ligand binding, regardless of whether the crystalline structure of the complex between the receptor and the ligand is known.

Such biosensors can be constructed using any type of protein, in particular proteins having cysteine residues which are important for their structure or their stability, and constitute novel tools for detecting, assaying and locating a large variety of ligands in a heterogeneous population of molecules.

A subject of the present invention is a biosensor, characterized in that it consists of (i) at least one fragment of a receptor which is protein in nature, capable of binding to a suitable ligand via an active site, and in which fragment at least one of its amino acid residues located in the proximity of said active site is naturally present in the form of a Cys residue, or is substituted with a Cys residue, and (ii) a fluorophore coupled to said Cys residue(s).

The Cys residues which are not essential, for example those which are located far from the active site, can be changed into other residues by site-directed mutagenesis, in particular into Ser or Ala residues, so as to avoid interference coupling with the fluorophores.

For the purpose of the present invention, the term "receptor" is intended to mean a protein macromolecule having an active site, capable of binding a ligand, in particular an antibody, a hormone or bacterial receptor, an affinity protein, a transport protein or a viral receptor or else any polypeptide having a specific affinity for a ligand.

For the purpose of the present invention, the term "ligand" is intended to mean any molecule capable of binding to said receptor via said active site, in particular a protein, peptide or hapten antigen, such as a bacterial antigen, or a hormone, a cytokine, an interleukin, TNF (Tumor Necrosis Factor), a growth factor, a viral protein, or a peptide or nucleotide sequence.

For the purpose of the present invention, the expression "active site of the receptor or of the receptor fragment" is intended to mean all of the residues which contribute to the binding of the ligand. This active site is also called binding site or paratope.

For the purpose of the present invention, the term "proximity" is understood to be as defined by the mathematical theory of topological spaces; the residues of the receptor which are in the proximity of the active site are the residues which are in direct contact with the ligand, those which are in contact by water molecules, and those for which the solvent accessible surface area (ASA; Creighton, 1993) is modified by the binding of the ligand. The use of spheres of increasing radius, from 1.4 to a maximum of 30 Å, preferably from 1.4 to 2.9 Å, that is to say greater than that of a water molecule (1.4 Å), for example 1.4, 1.7, 2.0, 2.3, 2.6 and 2.9 Å, to calculate the solvent accessible surface area, makes it possible to define an increasingly large proximity for the binding site of the receptor, and thus to increase the set of potential sites for coupling the fluorophore, taking into account the considerable volume of a fluorophore compared to that of a water molecule. The mutation to cysteine must not be greatly deleterious to the interaction with the ligand if the aim is for the labeled receptor to maintain good affinity for the ligand.

For the purpose of the present invention, the term "fluorophore" is intended to mean any molecule the fluorescence of which is sensitive to its microenvironment, and which can be coupled to a Cys residue.

According to an advantageous embodiment of said biosensor, said receptor has one or more disulfide bridges essential to its activity or to the maintaining of its structure.

According to an advantageous embodiment of said biosensor, said receptor is an antibody or an antibody fragment, such as an Fv, scFv or Fab fragment or a miniantibody; said antibody is advantageously a natural or artificial monoclonal antibody.

In accordance with the invention, the fluorophore is in particular selected from the group consisting of: IANBD, CNBD, acrylodan, 5-iodoacetamidofluorescein (5-IAF) or a fluorophore having an aliphatic chain of 1 to 6 carbon atoms.

According to another advantageous embodiment of said biosensor, the biosensor is in soluble form or is immobilized on a suitable solid support made of plastic material or glass.

According to yet another advantageous embodiment of said biosensor, said solid support is a microplate or an optical fiber.

Among the immobilization methods, mention may be made of those described in Piervincenzi et al., 1998; Yoshioka et al., 1991; Turkova, 1999; Saleemuddin, 1999; Weetall, 1993; Sara et al., 1996.

When the support is an optical fiber, such biosensors may be implanted in situ, for example into a vein of a patient or of an animal, or into an individual cell, so as to assay the ligand in vivo, continuously, and thus to follow its kinetics of appearance and disappearance.

The subject of the present invention is also a protein-based chip, characterized in that it consists of a solid support on which at least one biosensor according to the invention is immobilized.

Such protein-based chips comprise a solid support, for example a microplate, on which the molecules of various biosensors are advantageously immobilized in a matrix and included in microfluid circuits. Such biosensors make it possible to simultaneously and instantaneously detect and assay a large number of ligands in a sample, for example a sample of body fluid.

The biosensors according to the invention have a certain number of advantages:
the residue of the receptor on which the coupling of the fluorophore is carried out is predetermined and is a Cys residue located in the proximity of the active site of the receptor.

the coupling of the fluorophore on predetermined cysteine residues is carried out under conditions in which it does not attack the disulfide bridges possibly present on the receptor.

A subject of the present invention is also a method for preparing biosensors as defined above, characterized in that it comprises the following steps:

(a) selecting residues of the receptor by searching for the residues which, in the receptor-ligand complex, (i) are in direct contact with the ligand, or (ii) are in contact via a water molecule, or (iii) have a solvent accessible surface area (ASA) which is modified by the binding of the ligand, when use is made of spheres of increasing radius of 1.4 to 30 Å, preferably of 1.4 to 2.9 Å, for the molecule of said solvent;

(b) calculating the solvent accessible surface area (ASA), for the free receptor, of the atoms in the γ position and, optionally, in the δ position for each amino acid residue selected in (a), using a sphere of radius 1.4 Å (corresponding to a water molecule), and selecting the residues in which the atom in the γ position or the atom in the δ position is accessible to the solvent; the solvent accessibility of an atom in the δ position is informative with respect to that of the Sγ of a corresponding Cys residue. Conventionally, the accessibility threshold is fixed at a minimum of 2%, preferably at 20-25%, and more favorably greater than 25%;

(c) mutating by site-directed mutagenesis at least one of the residues selected in (b) to a Cys residue when said residue is not naturally a Cys residue, and (d) coupling the Sγ atom of at least one Cys residue obtained in (b) or (c) to a fluorophore. In this case, the Sγ atom of the Cys residue, which may or may not be a mutant residue, which is exposed to the solvent is the target for the fluorophore molecule. It is considered that the Sγ of the Cys residue, which may or may not be a mutant residue, superposes with the atom in the γ position of the wild-type residue. This atom in the γ position must therefore be exposed to the solvent in the structure of the wild-type receptor. When an atom is present in the δ position in the wild-type residue, it may mask the atom in the γ position, with respect to the solvent, whereas this masking will no longer exist after it has been changed into Cys.

According to an advantageous embodiment of said method, in step (b), the ASA values for a residue $X_i$ in the i position of the sequence of the receptor are expressed in the form of percentages of the corresponding ASA values in a tripeptide Gly-$X_i$-Gly, which would adopt the same configuration as the tripeptide $X_{i-1}$-$X_i$-$X_{i+1}$ in the structure of the receptor.

The residues selected in step (b) are divided into three classes:
the first class contains the residues in which the atom in the γ position is accessible to the solvent in the structure of the free receptor, and which are in contact with the ligand either directly or via a water molecule;
the second class contains the residues in which the atom in the γ position is accessible and which are not in direct contact with the ligand;
the third class contains the residues in which the atom in the δ position is accessible but not the atom in the γ position.

When the crystalline structure of one of the partners of the receptor/ligand pair, or of the complex thereof, is unknown or unavailable, in this case, said method comprises, prior to step (a) as defined above, a step of modeling the molecule for which the structure is unknown or unavailable: receptor or active fragment of this receptor (for example an antibody Fv fragment), its ligand (antigen), or the complex (receptor-ligand) thereof.

Advantageously, said modeling step is carried out via a computer-assisted method; mention may be made, for example, of the methods described in Sternberg, 1996; Rees et al., 1996.

As a variant, a subject of the present application is a method for preparing biosensors, which comprises the following steps:

($a_1$) identifying the active site of the receptor by mutagenesis of the set, or of a subset, of the residues of the receptor, and determining the variations in the parameters of interaction with the ligand ($K_D$, $k_{on}$, $k_{off}$) which are due to each mutation or to limited groups of mutations;

($b_1$) selecting the Cys residues, or the residues to be mutated to cysteine, from the residues of the receptor which are located in the proximity of the residues of the active site along the sequence;

($c_1$) mutating by site-directed mutagenesis at least one of the residues selected in ($b_1$) to a Cys residue when said residue is not naturally a Cys residue; and ($d_1$) coupling the Sγ atom of at least one Cys residue obtained in ($b_1$) or in ($c_1$) to a fluorophore.

For example, the sequences of the hypervariable loops of the antibody mAbD1.3, named CDRs (Complementary Determining Regions or regions which determine antibody-antigen complementarity), can be defined using sequence comparisons (England et al., 1999). The active site of mAbD1.3 for its interaction with lysozyme has been characterized by changing the residues of the CDRs, mainly to Ala (Dall'Acqua et al., 1996, 1998; England et al., 1997, 1999; Ito et al., 1993, 1995; Hawkins et al., 1993; Ysern et al., 1994; Goldbaum et al., 1996). The light (L) chain residue changes L-H30A, L-Y32A, L-Y49A, L-Y50A and L-Y92A increase the dissociation constant for the Fv or scFv fragment of mAbD1.3 and lysozyme, whereas the changes L-I29T, L-T51A, L-T52K, L-T53A, L-S93A and L-T97S affect it very little or not at all. Similarly, the heavy (H) chain residue changes H-F27N, H-Y32A, H-W52A, H-D54A, H-D100A, H-Y101A, H-R102K or H-R102M increase the dissociation constant whereas H-T30A, H-N56A, H-D58A and H-R99A affect it very little or not at all.

Consequently, the residues L-Thr51, L-Thr52, L-Thr53, L-Ser93, L-Thr94, H-Thr30, H-Asn56, H-Asp58 and H-Arg99, which are polar and therefore probably exposed at the surface of the antibody mAbD1.3 and which are close to the residues of the active site in the sequence, would constitute potential coupling sites according to purely functional criteria. Certain common potential sites are indeed found when criteria based on structure (points (a) and (b) of the general method, above) or on function (points ($a_1$) and ($b_1$) of the variant of said method, above) are used, for example L-Thr52, L-Thr53, L-Ser93, H-Thr30, H-Asn56, H-Asp58 and H-Arg99.

According to another advantageous embodiment of said method, prior to step (a) or to step ($a_1$), the nonessential Cys residues of the receptor are substituted with Ser or Ala residues by site-directed mutagenesis.

According to another advantageous embodiment of said method, in step (d) or in step ($d_1$), said fluorophore is selected from the group consisting of IANBD, CNBD, acrylodan, 5-iodoacetamidofluorescein or a fluorophore having an aliphatic chain of 1 to 6 carbon atoms.

According to another advantageous embodiment of said method, prior to step (d) or to step ($d_1$), the mutated receptor obtained in step (c) or in step ($c_1$) is subjected to a controlled reduction; in fact, the coupling yield may be significantly improved when the step is added.

According to yet another advantageous embodiment of said method, after step (d) or step ($d_1$), it comprises an additional step (e) or ($e_1$) for purifying the biosensor, for example on an exclusion or affinity column, in particular an immobilized nickel ion column when the receptor fragment or antibody fragment comprises a His-residue extension.

According to yet another advantageous embodiment of said method, after step (e) or step ($e_1$), it comprises an additional step for measuring the equilibrium constant ($K_D$ or $K'_D$) or the dissociation ($K_{off}$) and association ($k_{on}$) rate constants for the receptor and ligand.

The equilibrium constant is named $K_D$ when the complex is in solution and $K'_4D$ when one of the partners of the complex is immobilized.

Said constant may, for example, be determined from measurements of fluorescence by intensity or by anisotropy. All the data obtained ($K_D$, $K'_D$, $k_{off}$, $k_{on}$, size of change in fluorescence during ligand binding, shift of emission maximum) make it possible to refine the selection of the residues of the receptor which are the most suitable for coupling the fluorophore.

According to yet another advantageous embodiment of said method, after step (d) or ($d_1$) or step (e) or ($e_1$), it comprises an additional step for immobilizing the biosensor on a suitable solid support as mentioned above.

A subject of the present invention is also the use of said biosensors, alone or as a mixture, for applications comprising detecting, assaying and locating ligands.

The biosensors according to the invention make it possible, for example, to detect, assay or locate an antigen or a hapten in a heterogeneous population of molecules, instantaneously.

In the health domain, said biosensors are of use:
- for monitoring the progression or the regression of a disease, in response to a treatment;
- for assaying an infectious agent (bacterium, virus), a pathogenic agent (tumor cell), a macromolecule (hormone, cytokine) or a hapten in a body fluid (for example blood, sperm, etc.);
- for determining the serotype of an infectious agent;
- for detecting a cellular marker and determining its location;
- for sorting cells, on the basis of the presence of a surface marker;
- for sorting molecules;
- for quantifying an intracellular or extracellular component, monitoring its kinetics of appearance and disappearance and monitoring its location;
- for determining the half-life of a molecule (depending on its instability, on its metabolism or on its elimination), its diffusion and its tissue concentration;
- for monitoring the effect of a chemical molecule on a cellular component (screening libraries, in particular protein libraries).

In the domain of the environment, of industry and of suppression of fraud, said biosensors are also of use:
- for detecting and assaying a pollutant, and monitoring its elimination, by natural bioremediation processes;
- for assaying an active component in a preparation being produced or marketed;
- for monitoring the kinetics of a chemical synthesis reaction.

Said biosensors are also of use in producing protein-based chips.

The subject of the present invention is also reagents for detecting, assaying and/or locating ligands, characterized in that they comprise at least one biosensor as defined above.

A subject of the present invention is also a method for detecting, assaying or locating a ligand in a heterogeneous sample, characterized in that it comprises bringing said heterogeneous sample into contact with at least one reagent according to the invention.

A subject of the present invention is also a kit for detecting, assaying and/or locating ligands, characterized in that it includes at least one reagent according to the invention.

A subject of the invention is also a kit for screening for inhibitors of the ligand/receptor interaction, characterized in that it includes at least one biosensor according to the invention.

A subject of the present invention is also the use of the plasmid pMR1 of sequence SEQ ID NO:10, deposited with the Collection Nationale de Culture de Mircoorganismes (CNCM) [National Collection of Cultures and Microorganisms], under the number I-2386, dated Feb. 29, 2000, for preparing a biosensor in accordance with the invention.

A subject of the present invention is also the use of the plasmid pMR1(VL-S93C) of sequence SED ID NO:11, deposited with the Collection Nationale de Culture de Microorganismes (CNCM), under the number I-2387, dated Feb. 29, 2000, for preparing a biosensor in accordance with the invention.

A subject of the present invention is also the plasmid pMR1 of sequence SEQ ID NO:10, deposited with the Collection Nationale de Culture de Microorganismes (CNCM), under the number I-2386, dated Feb. 29, 2000.

A subject of the present invention is also the plasmid pMR1 (VL-S93C) of sequence SEQ ID NO:11, deposited with the Collection Nationale de Culture de Microorganismes (CNCM) under the number I-2387, dated Feb. 29, 2000.

Besides the above arrangements, the invention also comprises other arrangements, which will emerge from the following description, which refers to examples of implementation of the method which is the subject of the present invention, and also to the attached drawings, in which:

FIG. 1 illustrates the criteria for determining the residues of the Fv fragment of the antibody named mAbD1.3, in the proximity of the active site for binding to lysozyme, which can be used for coupling the fluorophore. Columns 1 and 2 indicate the residues of the Fv fragment of the antibody named mAbD1.3 which are in direct contact with the lysozyme, either at least via their side chain (d), or via their peptide chain (b); those which are in contact via water molecules (i), and those in which the solvent accessible surface area (ASA) is modified by the binding of the lysozyme when spheres of radius 1.4, 1.7, 2.0, 2.3, 2.6 or 2.9 Å are used for the molecule of solvent. Columns 3 and 4 indicate the ASA values, in the free Fv (using R=1.4 Å), of the atoms in the γ position and, optionally, δ position of each of the residues $X_i$ selected, in the i position of the sequence of the Fv, in the form of percentages of the corresponding ASAs in a tripeptide Gly-$X_i$-Gly which would adopt the same conformation as the tripeptide $X_{i-1}$-$X_i$-$X_{i+1}$ in the structure of the Fv. Columns 5, 6 and 7 indicate the ASA, in the structure of the native complex, of the groups in the γ, δ and ε positions in the initial side chain. Columns 8 and 9 indicate the mutations of these residues known in mAbD1.3 and their effects, in the form of a variation ΔΔG of energy of interaction with lysozyme. Column 10 summarizes the classification of the residues in order of decreasing priority; (+) corresponds to the residues in which the atom in the γ position is accessible to the solvent in the structure of the free Fv, and which are in contact with the lysozyme either directly or via a water molecule in the structure of the complex, (+/−) corresponds to the residues in which the atom in the γ position is accessible and which are not in direct contact with the lysozyme, and (?) corresponds to the residues in which the atom in the δ position is accessible but not the atom in the γ position.

FIG. 2 illustrates the optimization of the production of recombinant mAbD1.3 Fv (scFv-His6) using prokaryotic expression vectors (pMR1 and pMR5). The periplasmic content of E. Coli strains HB2151 and BL21 (DE3) transformed, respectively, with the plasmids pMR5 and pMR1, induced by IPTG (BL21 (DE3)) or anhydrotetacyclin (HB2151) and cultured while varying the temperature, the induction time and the inducer concentration, was measured by ELISA using an anti-His5 antibody. The results are expressed in arbitrary units.

FIG. 3 illustrates the analysis, by SDS-polyacrylamide gel electrophoresis and Coomassie blue staining, of the fractions from the purification of the mutant scFv-His6(VL-S93C) on a nickel ion column. EP: unpurified periplasmic extract, NR: fractions not retained, M: molecular mass marker, $L_{20}$ and $L_{40}$: fractions from washing with 20 and 40 mM of imidazole, EL: elution fractions.

FIGS. 4 and 5 illustrate the noncovalent oligomerization of the wild-type scFv-His6 and of the VL-S93C mutant, analyzed by size exclusion chromatography. The purified scFv-His6s were injected at a concentration of 50 μg/ml for the wild-type and for the mutant, in a volume of 200 μL, at the top of a Superdex® 75 HR 10/30 column (Pharmacia). The chromatogram was developed at 25° C., at pH=7.5 for the wild-type and at pH=7.0 for the mutant.

FIG. 9 shows the evolution of the coupling yield (proportion of mutant scFv-His6s linked to a fluorophore, here IANBD) and of the material yield when the biosensor is prepared, as a function of the concentration of 2-mercaptoethanol used for the controlled reduction.

Figure 11:
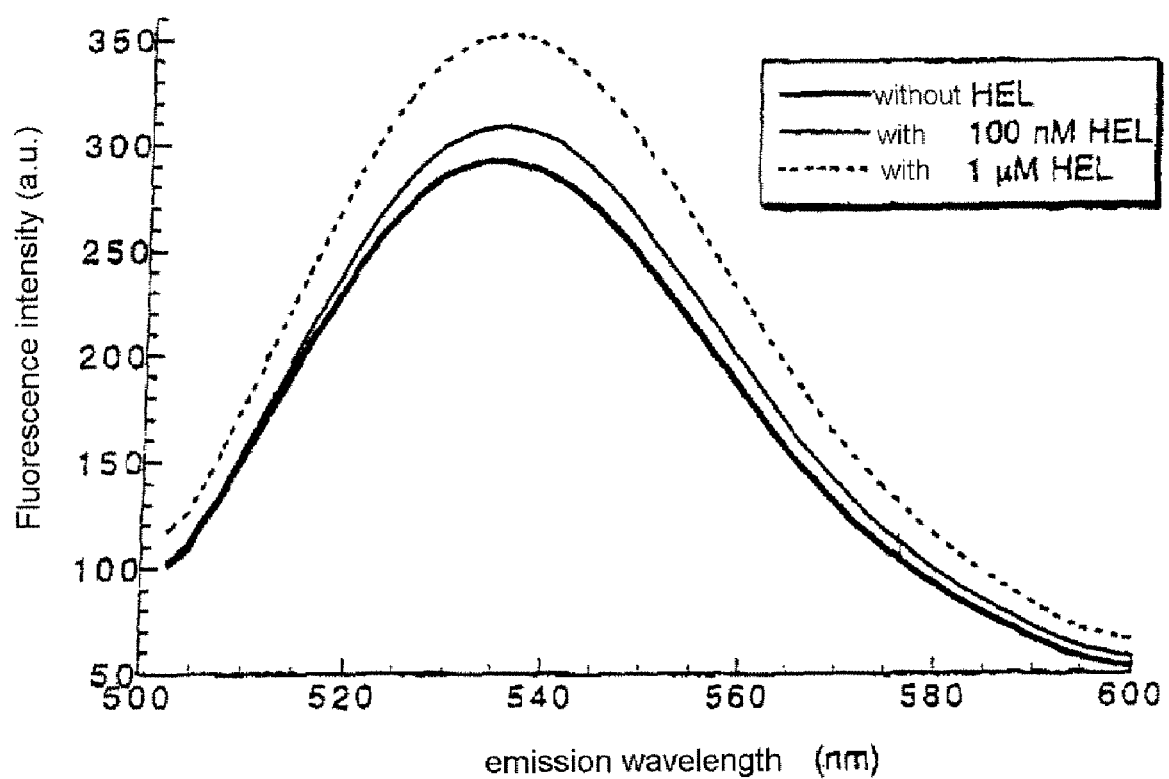

FIG. 11 illustrates the fluorescence emission by the scFv-His6(VL-S93ANBD) derivative for an excitation at 469 nm expressed in arbitrary units (a.u.). The spectra were recorded in the absence of lysozyme, or 1 minute after addition of lysozyme at 100 nM and 1 μM (final concentrations) and brief homogenization. The same maximum enhancement of fluorescence (+27%) is observed for three different preparations of this same derivative, for which various coupling methods (with or without prior reducing treatment) were used, and various coupling yields were obtained.

Figure 12:
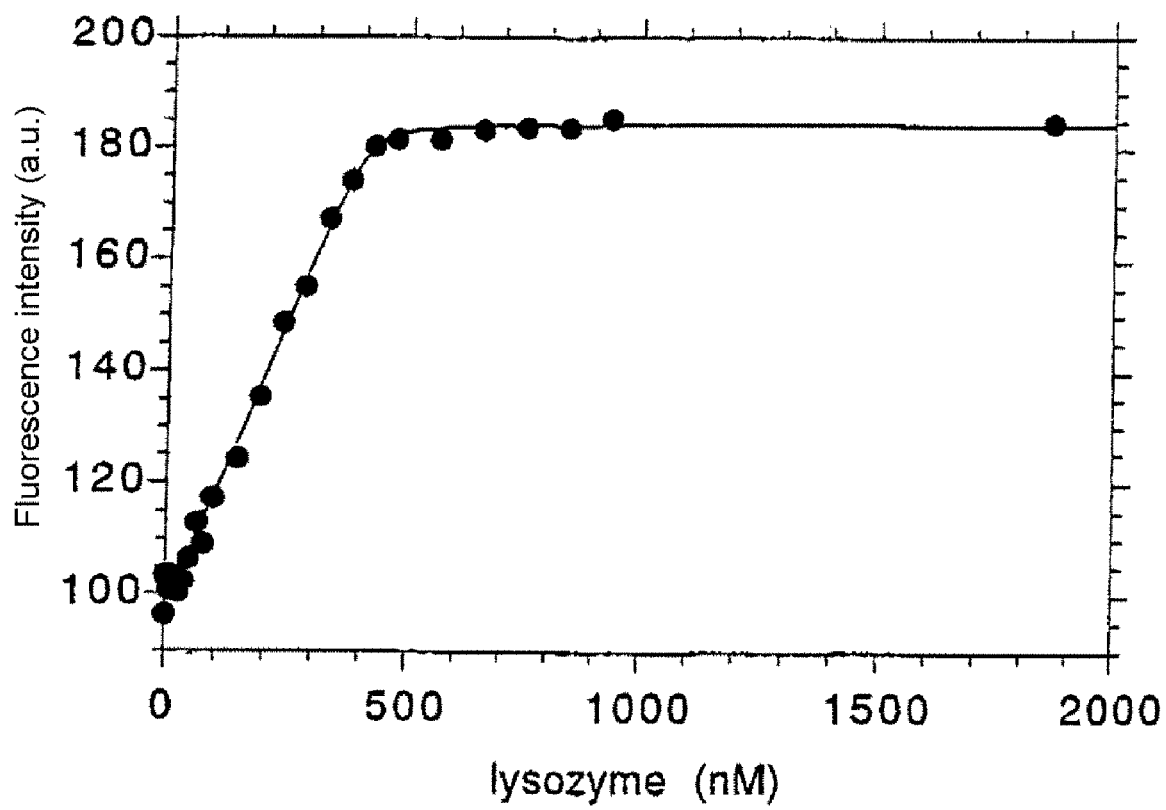

FIG. 12 illustrates the fluorescence emission at 535 nm by the scFv-His6(VL-S93ANBD) conjugate, for an excitation at 480 nm, expressed in arbitrary units (a.u.). The fluorescence intensities were recorded in the absence or in the presence of varying concentrations of lysosyme (10 nM to 2 µM) in a 50 mM Tris-HCl, 150 mM NaCl buffer, pH=7.5. In this buffer, the fluorescence intensity of the scFv-His6(VL-S93ANBD) conjugate is proportional to the concentration of lysozyme up to 400 nM and increased by 91% at saturation. The curve obtained makes it possible to directly titrate the lysozyme between 10 and 400 nM.

FIG. 13 illustrates the coupling yields and the fluorescence properties of the biosensors. Column 1 indicates the residues of the Fv fragment of the antibody named mAbD1.3 which have been mutated to Cys residues; these residues were chosen as a function of the structural data set out in FIG. 1. Column 2 indicates the percentage of molecules of the mutant scFv-His6 which are coupled to the IANB, compared with the wild-type (wt) scFv-His6. Column 3 indicates the variation in fluorescence at 535 nm between the free forms and the forms complexed with lysozyme of the scFv-Cys-ANBD conjugates, measured in a 20 mM Tris-HCl, 500 mM NaCl, 160 mM imidazole buffer, pH=7.9. Considerable enhancements of fluorescence are obtained for more than half the coupling positions.

It should be clearly understood, however, that these examples are given only by way of illustration of the subject of the invention, of which they in no way constitute a limitation.

EXAMPLE 1

Materials And Methods

1-Parental Bacterial Strains, Plasmids and Phages

TABLE 1

| Strain | Main characteristics | Reference |
| --- | --- | --- |
| HB2151 | Ara Δ(lac-pro) thi/F' proA⁺B⁺ lacI$^q$ZΔM15 | Carter et al., 1985 |
| RZ1032 | Hfr dut ung r⁺ m⁺ | Kunkel et al., 1987 |
| BL21(DE3) | F⁻ ompT hsdS$_B$(r$_B^-$, m$_B^-$) gal dcm/lambdaDE3 | Studier and Moffatt, 1986 |

The vector pASK98-D1.3 encodes a hybrid between an scFv of the monoclonal antibody mAbD1.3 and a tag of the streptavidin type. The corresponding gene is under the control of the tetracycline promoter and operator (Skerra, 1994). pSPI1.0 is a derivative of pET26b (Novagen) and allows scFvs to be subcloned under the control of the T7 phage promoter.

2-Culture Media and Buffers

LB and 2xYT media have been described (Sambrook et al., 1989). SB medium contains 16 g/l bactotryptone, 10 g/l bactoyeast, 10 g/l NaCl, 50 mM K$_2$HPO$_4$, 5 mM MgSO$_4$ and 1% glucose (Plückthun et al., 1996). Ampicillin is used at 200 µg/ml and kanamycin at 30 µg/ml in the growth media. PBS and TBE buffers have been described (Sambrook et al., mentioned above). Buffer P: 20 mM Tris-HCl, pH 7.9; 500 mM NaCl. Buffer Q: 50 mM Tris-HCl, pH 7.5; 150 mM NaCl. Buffer C: 50 mM sodium phosphate pH 7.0; 150 mM NaCl.

3-Oligonucleotides

The sequences of the oligonucleotides used for the mutagenesis or the genetic constructs are given in the following table. The modified codons are marked in bold for the mutagenic oligonucleotides.

TABLE II

| Name | Sequence | |
| --- | --- | --- |
| pMR1-VL-H30C | 5'-atggtacgatttattaaacat tataagggtg-3' | SEQ ID NO:20 |
| pMR1-VL-N31C | 5'-catgctaaataacagtggata ttcccacttg-3' | SEQ ID NO:17 |
| pNR1-VL-Y49C | 5'-agacgattccaacaacatata cactggtcctcga-3' | SEQ ID NO:21 |
| pMR1-VL-Y50C | 5'-gattccaacaacatatctggt cctcgactcctcta-3' | SEQ ID NO:22 |
| pMR1-VL-T52C | 5'-catctgctaaggtacatgtat aatagac-3' | SEQ ID NO:13 |
| pMR1-VL-T53C | 5'-catcgctaagcatgttgtata ataga-3' | SEQ ID NO:1 |
| pMR1-VL-D56C | 5'-cttgatggcacaccgcatgct aaggttgttg-3' | SEQ ID NO:16 |
| pMR1-VL-W592C | 5'-gaggagtacgcaaaaatgttg acagtaa-3' | SEQ ID NO:12 |
| pMR1VL-S93C | 5'-cgaggagtacaccaaaaatgt tgacagta-3' | SEQ ID NO:2 |
| pMR1-VL-T94C | 5'-cgtccgaggacaactccaaaa atgtt-3' | SEQ ID NO:3 |
| pMR1-VH-S28C | 5'-acaccatagccagttaagcag aaccctgagacg-3' | SEQ ID NO:18 |
| pMR1-VH-G31C | 5'-caagagtaattggacaatacc acatttg-3' | SEQ ID NO:24 |
| pMR1-VH-T30C | 5'-acaccatagccgcataatgag aaccctg-3' | SEQ ID NO:15 |
| pMR1-VH-Y32C | 5'-cagtttacaccacacccggtt aatgaga-3' | SEQ ID NO:14 |
| pMR1-VH-G53C | 5'-acccttactaaacacaactac ctttgtgtctg-3' | SEQ ID NO:25 |
| pMR1-VH-N56C | 5'-ttatagtctgtgcacccatca ccccaaatcat-3' | SEQ ID NO:19 |
| pMR1-VH-R99C | 5'-tgacacggtctctcacactaa tatccgaactgatga-3' | SEQ ID NO:23 |
| Sequencing: | | |
| VL-CDR1-Rev | 5'-agaatattgtgttcctga-3' | SEQ ID NO:4 |
| VH-CDR1-Rev | 5'-tgctgatgctcagtctgg-3' | SEQ ID NO:5 |
| VH-Seq-CDR-3 | 5'-ggtgatggaaacacagac-3' | SEQ ID NO:6 |
| pASK98-seq-His | 5'-cgccgcgcttaatgc-3' | SEQ ID NO:7 |
| Construction | | |
| pASK98-His6-For: | 5'-tcgagatcaagcggccgctgg aacaccatcaccat-3' caccatta-3' | SEQ ID NO:8 |
| PASK98-His6-Back: | 5'-agcttaatggtgatggtgatg gtggtccagcggcc-gcttgat c-3' | SEQ ID NO:9 |

4-Recombinant DNA Techniques

Preparation of plasmid DNA: the plasmid DNA minipreparations are carried out using 5 ml of bacterial culture, by the alkaline lysis method (Sambrook et al., mentioned above). The midipreparations are carried out using 30 to 60 ml of culture, with the QIAFILTER™ Plasmid Midikit (QIAgen).

Transformation: the preparation of competent bacteria by the simple $CaCl_2$ method and the transformation by heat shock are carried out as described in Sambrook et al., mentioned above.

Purification of DNA fragments by electrophoresis: the restriction mixture is loaded onto a 1 to 2% agarose gel (Easy Bag Agarose, Quantum Bioprobe). The electrophoresis is performed for 1 to 2 hours at 8 V/cm in TBE buffer. The gel is then stained with ethidium bromide at 1 µg/ml in water. The agarose band containing the DNA fragment is cut out under a UV lamp and the DNA is then extracted and purified using the QIAQUICK® Gel Extraction Kit (QIAgen).

Ligation of a DNA fragment into a plasmid vector: for the ligation of restriction fragments, the mixture thereof is precipitated with Precipitator (Appligene), resuspended in water and then brought to 50° C. for 5 minutes. 400IU of T4 DNA ligase (New England Biolabs) and its buffer are added and the ligation is continued overnight at 16° C. The HB2151 strains are then transformed with the ligation products.

Mutagenesis: the site-directed mutagenesis is carried out as described in Kunkel et al., (1987) using T4 polynucleotide kinase, T4 DNA ligase and T4 DNA polymerase (New England Biolabs).

Sequencing: the presence of a mutation or the genetic constructs are verified by sequencing, using the T7-Sequencing Kit (Pharmacia), with the nucleotide mixtures for short reading, the dATP-$^{35}$S and a primer. The matrix consists of a minipreparation of plasmid DNA, denatured with sodium hydroxide and then neutralized by passing it over a Microspin S-400-HR column. The sequence gels (6% acrylamide 1:19 bis, 42% urea in TBE, 30×40 cm) are subjected to a preelectrophoresis for 45 min at 40 W, and then loaded with the preboiled samples (Sambrook et al., mentioned above). The migration is performed at 40 W for 2 to 3 h. The gels are dried and exposed overnight with a BIOMAX® MR film (Kodak).

5-Recombinant Plasmid Constructions pMR1: the vector pASK98-D1.3 is cleaved with the XhoI and HindIII enzymes. The restriction mixture is passed over a Microspin S-400-HR column so as to remove the smallest restriction fragment (43 bp). The oligonucleotides pASK98-his6-for and pASK98-his6-back are phosphorylated and hybridized at 60° C. so as to form a linker with sticky ends, which is inserted into the large XhoI-HindIII fragment of pASK98-D1.3. The phagemid obtained, pMR1, is controlled by restriction analysis with the NotI and PvuI enzymes and by sequencing using the oligonucleotide pASK98-seq-His6; it corresponds to SEQ ID NO: 10.

PMR 5: the plasmids pFBX and pSPI1.0 are cleaved with SfiI and NotI. The small fragment of PFBX (750 bp) containing the gene of the D1.3 scFv and the large fragment of pSPI1.0 (4650 bp) are purified on agarose gel and then assembled by ligation. The plasmid obtained, pMR5, is controlled by restriction analysis with the AflIII enzyme.

6-Production of Antibody Fragments

Production of a small amount from pMR1 or pMR5: 200 ml of 2xYT ampicillin medium are inoculated with an isolated colony of the recombinant strains HB2151(pMR1) or BL21(DE3, pMR5). The culture is shaken at 22, 30 or 37° C. until an $A_{600nm}$=0.5 is obtained, at which point it is induced with 0.2 to 1.0 µg/ml of anhydrotetracycline for HB2151 or with 0.2 to 1.0 mM of IPTG for BL21(DE3), and the shaking is then continued for 2 h, 5 h or 16 h. A periplasmic extract is prepared by osmotic shock (see below) using 50 ml of culture centrifuged for 20 min at 10, 500 g, at 4° C.

Production of large amounts: to produce the scFv-His6s, SB medium (100 ml) supplemented with ampicillin is inoculated with an isolated colony of the recombinant strain HB2151(pMR1). The culture is shaken overnight at 37° C. and then 25 ml of the contents are transferred into 750 ml of the same medium preequilibrated at 22° C. The culture is shaken at 22° C. until an $A_{600nm}$=2.0 is obtained, and is then induced with 0.22 µg/ml of anhydrotetracycline. The growth is continued for approximately 2 h 30 min, until an $A_{600nm}$=4 is obtained. The culture is centrifuged for 20 minutes at 9500 g, at 4° C. The periplasmic extract is prepared using the polymyxin method described below (example 1-7).

7-Preparation of Periplasmic Extracts

The bacterial cultures are centrifuged and periplasmic extracts are prepared from the bacterial pellets using one of the following four methods. The volumes are indicated relative to the volume of culture treated.

Osmotic shock method: the bacterial pellet is resuspended in 20% sucrose in 100 mM Tris HCl, pH 7.5 ($\frac{1}{20}^{th}$ volume). The suspension is maintained on ice for 10 minutes and then centrifuged for 15 minutes at 10,000 g, at 4° C. The pellet is taken up in 0.5 mM $MgCl_2$ ($\frac{1}{20}^{th}$ volume). The suspension is again maintained on ice for 10 minutes and centrifuged in the same way. This second supernatant constitutes the actual periplasmic extract. The first supernatant may, however, be used after dialysis against buffer P.

Tris-EDTA method: the bacterial pellet is resuspended in 100 mM Tris-HCl, pH 7.5; 1 mM EDTA ($\frac{1}{20}^{th}$ volume). The suspension is homogenized for 30 minutes by magnetic stirring at 4° C., and then centrifuged for 30 minutes at 35,000 g. The supernatant constitutes the periplasmic extract. The pellet is resuspended in $\frac{1}{20}^{th}$ volume of SDS at 1% in water. It contains the insoluble, membrane-bound or cytoplasmic proteins.

Tris-EDTA-NaC method: this method is identical to the Tris-EDTA method, except that the bacterial pellet is resuspended in 100 mM Tris-HCl, pH 7.5; 1 mM EDTA and 1 M NaCl.

Polymyxin method: this method is identical to the Tris-EDTA-NaCl method, except for the single difference that the bacterial pellet is resuspended in buffer P containing 1 mg/ml of polymyxin B sulfate (ICN).

8-Purification of Antibody Fragments

Purification of the scFv-His6s: the periplasmic extract is filtered through a Millex filter (porosity of 0.45 µm, Millipore) and then loaded onto a column containing 1.5 ml of Ni-NTA Superflow resin (QIAgen) equilibrated with 10 ml of buffer P. The column is successively washed with 10 ml of 5 mM imidazole, 20 mM imidazole and 40 mM imidazole in buffer P. The scFv-His6s are eluted with 4×1.5 ml of 100 mM imidazole in buffer P. The elution fractions are analyzed by SDS-15% PAGE, according to the protocol described in example 1-10. Their protein concentration is measured either by means of a Bradford reagent (BioRad) using bovine serum albumin (BSA) as the standard, or by means of $A_{280nm}$, taking $\epsilon$=51,130 $M^{-1}.cm^{-1}$, calculated as described in Pace et al. (1995).

9-Quantification of scFv-His6 by Indirect ELISA

A microtitration plate (Nunc) is coated with hen egg white lysozyme (HEL, 10 µg/ml) in 50 mM $NaHCO_3$ buffer, pH 9.6, and incubated overnight at ambient temperature. The plate is saturated for 2 h at 37° C. with BSA (3% weight/volume) in PBS. The samples are diluted at least 2-fold in PBS containing 3% BSA, loaded onto the plate and left at ambient temperature for 1 h. The plate is washed 5 times with PBS containing 0.05% Tween 20, and then incubated for 1 h in the presence of a primary antibody (mouse anti-His5 monoclonal antibody, QIAgen) diluted to 0.2 µg/ml in PBS containing 3% BSA. The plate is washed as previously, and then incubated for 1 h in the presence of a secondary antibody (anti-mouse Fc monoclonal antibody coupled to alkaline phosphatase) diluted to 1/10,000. The plate is washed as previously and the immunocomplexes are revealed with 2 mg/ml of p-nitrophenylphosphate (Sigma) in 1M diethanolamine-HCl, pH 9.8, 10 mM $MgSO_4$. The $A_{405nm}$ signal is measured on a Labsystem Multiskan MS microplate reader. Under the experimental conditions used, the region of linearity is obtained for scFv-His6 concentrations of less than 0.8 µg/ml.

10-Electrophoresis of Proteins and Western-Blotting Techniques

SDS-PAGE: The stacking gel is a 4% acrylamide:bisacrylamide (1:29) gel in 125 mM Tris-HCl, pH 6.8; 0.1% SDS, and the separating gel is a 15% acrylamide gel in 375 mM Tris-HCl, pH 8.8; 0.1% SDS. The electrophoresis buffer contains 190 mM glycine, 2 mM Tris-base and 0.1% SDS. The gels (8×7 cm) are poured and the electrophoresis is carried out using a Hoefer Mighty Small II apparatus. 2× loading buffer (125 mM Tris-HCl, pH 8.0; 2.5% SDS; 20% glycerol; 2 mg/ml bromophenol blue, and 10% 2-mercaptoethanol in the case of reducing SDS gels) is added to the samples, which are heated for 5 min at 90° C. before being loaded. The electrophoresis is performed for 1 h 30 at 30 mA. The markers have the following molecular masses: 21.5; 31; 45; 66.2 and 97.4 kDa (Prestained Molecular Weight Marker low range, Bio-Rad). The proteins are revealed by staining the gel in a bath of 1 mg/ml Coomassie blue R250, 42% methanol, 16% acetic acid, and then destaining in several baths of 40% methanol, 10% acetic acid.

Western-blotting technique: the proteins are separated by SDS-PAGE and then transferred onto a Hybond-C nitrocellulose membrane (Amersham) overnight, under 10V, in a chamber consisting of a TE22 Series Transphor Electrophoresis Unit HSI (Hoefer), containing 25 mM Tris-base, 190 mM glycine, 20% methanol. Next, the membrane is saturated with 3% BSA (weight:volume) in TBS buffer (100 mM Tris-HCl, pH 7.5; 150 mM NaCl), and then incubated for 1 h at ambient temperature with the primary and secondary antibodies, diluted in TBS containing 3% BSA, at the concentrations described for the ELISA (example 1-9). After each incubation with an antibody, the membrane is washed in two baths of TTT buffer (200 mM Tris-HCl, pH 7.5; 500 mM NaCl; 0.05% Tween 20; 0.2% Triton X-100) followed by a bath of TBS buffer. The proteins are revealed by incubating the membrane in 100 mM Tris-HCl, pH 9.5; 100 mM NaCl; 50 mM $MgCl_2$; 0.4 mg/ml Nitro Blue Tetrazolium (Sigma) and 0.2 mg/ml 5-bromo-4-chloro-3-indolyl phosphate (Sigma). The revelation is stopped by immersing the membrane in water.

11-Analysis of the Interaction Between mAbD1.3 scFv and Hen Lysozyme using BIACORE™

The measurements are made on a CM5 chip (BIACORE™) with carboxymethyldexran surface, as described in England et al., (1999). Briefly, the lysozyme is immobilized in a channel by amide bonding up to a level of 500 RU (1 $RU=1$ ng/mn²). The rate constants for association ($k_{on}$) and for dissociation ($K_{off}$) at the interface, and also their $K'_D$ (dissociation constant at the interface) ratio, are measured at 20° C. with a flow of 10 µmin of scFv-His6 in PBS buffer supplemented with 0.005% Tween 20. The buffer also contains 1 µM of lysozyme during the dissociation phase in order to avoid re-binding of the scFv-His6s to the immobilized lysozyme. A channel with no immobilized lysozyme gives the nonspecific binding signal.

12-Exclusion Chromatography

The scFv-His6 is dialyzed against buffer Q and then concentrated by ultrafiltration through a CENTRICON® 10 (Amicon). The chromatographies are performed using a SUPERDEX® 75 HR10/30 column (Pharmacia), in buffer Q, at a flow rate of 0.5 ml/min. The column is preequilibrated under the same conditions. The proteins are detected in the effluent of the column using $A_{280nm}$. The samples, prepared in buffer Q, are injected using a 200 µl loop. They have the following compositions: scFv-His6, 200 µl at 50 µg/ml; BSA, 40 µg; chymotrypsinogen, 14 µg acetone, 0.1%. The ratio of the dimmer concentration to the monomer concentration is determined from the surface area of the peaks obtained.

13-Coupling of Fluorophores to the Free Cysteine of a Mutant scFv-His6

The mutant scFv-His6s freshly purified and rigorously conserved at 4° C. are dialyzed overnight against buffer C. Alternatively, the purified mutant scFv-His6s are adjusted to a concentration of at least 100 µg/ml by ultrafiltration through a CENTRICON® 10 filter (Amicon) and then reduced by addition of 2-mercaptoethanol at a final concentration of 1.1 mM, 1 mM, 10 mM or 50 mM. The mixture is incubated for 1 hour at 22° C. The reduced protein is separated from the excess reducing agent by desalting, using a HITRAP™ Desalting column (Pharmacia) preequilibrated in highly degassed buffer C.

The coupling is carried out by addition of NBD chloride, of ester of IANBD, of 5-IAF or of acrylodan (BioProbe) in a molar ratio (protein:fluorophore) of at least 1:20. The mixture is incubated for 24 hours at 22° C. and then centrifuged for at least 15 minutes at 10,000 g, at 4° C. The labeled scFv-His6 is then repurified. For this, the reaction mixture is diluted 7-fold in 5 mM imidazole in buffer P and successively loaded 3 times onto a column containing 500 µl of Ni-NTA resin. The excess fluorophore is removed by washing 6 times with 5 ml of 5 mM imidazole in buffer P. The labeled scFv-His6 is eluted with 1 ml of 40 mM imidazole in buffer P and then either with 4 times 500 µl of 100 mM imidazole in buffer P or with 3 times 600 µl of 160 mM imidazole in buffer P. A reference sample is obtained by treating buffer C alone in an identical manner. It is used as a control for the protein assays and the fluorescence measurements. The coupling yield may be estimated by the ratio of the fluorophore absorbance to the protein absorbance: $\epsilon 280$ nm(scFv-His6)=51.13 $mM^{-1}.cm^{-1}$, $\epsilon 435$ nm (CNBD)=9.6 $mM^{-1}.cm^{-1}$, $\epsilon 500$ nm (IANBD)=31.1 $mM^{-1}.cm^{-1}$, $\epsilon 492$ nm (5-IAF)=75 $mM^{-1}.cm^{-1}$, $\epsilon 391$ nm (acrylodan)=20 $mM^{-1}.cm^{-1}$, as described in Haugland et al., (1996).

EXAMPLE 2

Example of Implementation of the Method According to the Invention

1-Search for Residues of the Free Fv Fragment of mAbD1.3 which can be Used for Coupling the Fluorophore (FIG. 1)

The structure of the free Fv fragment of mAbD1.3 and that of the complex thereof with lysozyme are known (Bhat et al., 1994). However, in order to simplify the search for the residues of the Fv which are located in the proximity of the active site for binding to the lysozyme and which can be used for coupling the fluorophore, and so as to make this research applicable to other pairs of macromolecules for which only the structure of the complex exists, experimental data regarding the free Fv of mAbD1.3 were not used. A structural model of the free Fv was constructed by deleting the crystallographic coordinates for lysozyme from the structure of the complex. The structures were analyzed with the WHAT IF series of programs (Vriends, 1990; http://www.sander.embl-heidelberg.de/whatif/). The following principles were used:

1- Three types of residue were sought in mAbD1.3: those which are in direct contact with the lysozyme, those which are in contact via a water molecule, and those for which the solvent accessible surface area (ASA) is modified by the binding of the lysozyme when spheres of radius 1.4, 1.7, 2.0, 2.3, 2.6 or 2.9 Å are used for the molecule of solvent. The use of radii greater than that of a water molecule (1.4 Å) makes it possible to define an enlarged proximity for the antigen at the surface of the antibody and to take into account the considerable volume of a fluorophore compared to that of a water molecule. The residues of mAbD1.3 which satisfy one of these criteria, and the nature of the criterion used, are indicated in columns 1 and 2 of FIG. 1. Columns 8 and 9 of FIG. 1 give the nature of the known mutations in mAbD1.3 and their effects, in the form of a variation $\Delta\Delta G$ of energy of interaction with the lysozyme;

2- The residues of the receptor which are selected in (1) must be changed to Cys by mutagenesis, and then coupled to the fluorophore. The Sγ atom of the mutant Cys residue must therefore be exposed to the solvent in the free Fv, so that it can be attacked by the fluorophore molecule. It may be supposed, in a first approximation, that the Sγ of the mutant Cys residue superposes with the atom in the γ position of the wild-type residue. This atom in the γ position must therefore be exposed to the solvent in the structure of the wild-type free Fv. When an atom is present in the δ position in the wild-type residue, it may mask the atom in the γ position, with respect to the solvent, whereas this masking will no longer exist after it has been changed to Cys. It has therefore been considered that the solvent accessibility of an atom in the δ position may be informative with respect to that of the Sγ of the mutant Cys residue. The ASA values for the atoms in the γ and, optionally, δ position, for each residue selected in point 1) , are given in columns 3 and 4 of FIG. 1 (using R=1.4 Å);

3-The fluorophore may advantageously be coupled to the Sγ of the Cys residue via an aliphatic chain, the length of which varies from 1 to 6 carbon atoms for the most common fluorophores, but may be longer. After coupling, the polar and aromatic groups of the fluorophore should preferentially be at the periphery of the interface of contact between the antibody and the antigen, and not within this interface, where they would be in conflict with the antigen. For this, the aliphatic arm of the fluorophore must have access to the solvent in the structure of the complex between the labeled antibody and the antigen. In a first approximation, this condition is satisfied if one of the groups which are located in the γ, δ and ε positions in the initial side chain is accessible to the solvent in the structure of the native complex. The ASA for these groups of side chains is given in the same format as in point 2), in columns 5, 6 and 7 of FIG. 1;

4-The mutations of the residues of the receptor should not be too deleterious for the interaction with the antigen if the intention is for the labeled antibody to maintain a sufficient affinity. Columns 8 and 9 of FIG. 1 give the nature of the known mutations in mAbD1.3 and their effects, in the form of a variation ΔΔG of energy of interaction with the lysozyme (England et al., 1997 and 1999; Hawkins et al., 1993; Dall'Acqua et al., 1996; Dall'Acqua and Carter, 1998).

Column 10 of FIG. 1 summarizes the criteria used. The residues selected are divided into three classes of different priority. The first class contains the residues in which the atom in the γ position is accessible to solvent in the structure of the free Fv, and which are in contact with the lysozyme either directly or via a water molecule: VL-Thr53, VL-Ser93, VL-Thr94 and VH-Thr30. The second class contains the residues in which the atom in the γ position is accessible and which are not in direct contact with the lysozyme: VL-Asn31, VL-Thr52, VL-Asp56, VH-Ser28, and VH-Asn56. The third class contains the residues in which the atom in the δ position is accessible, but not the atom in the γ position: VL-Asn28, VL-His30, VH-Asp58 and VH-Arg99.

2-Construction of scFv-His6 Expression Vectors and Optimization of the Production of scFv-His6 (FIG. 2)

a) Construction of scFv-His6 Expression Vectors

The effect of coupling fluorophores to residues of the scFv of mAbD1.3 as defined in 1, on the binding to the lysozyme, was studied using recombinant mAbD1.3 scFvs having a C-terminal extension of 6 histidine residues (scFv-His6), expressed using prokaryotic expression vectors. The wild-type form and also the mutated forms of scFv were expressed and purified on a nickel column.

Two vectors which encode scFv-His6, pMR1 and pMR5, were constructed according to the protocol described in example 1-5. They carry the kanamycin resistance gene or ampicillin resistance gene, the M13 phage origin of replication (f1IG), and periplasmic addressing sequences, derived from the pelB or ompA genes, upstream of the scFv gene. The vector pMR5 carries the scFv-His6 gene under the control of a T7 phage promoter and of the lactose operator, in the lactose repressor gene. Expression is carried out in the BL21(DE3) strain which carries the T7 RNA polymerase gene under the control of the lacOlacp(UV5) promoter/operator on the λDE3 prophage. The addition of IPTG to the culture medium induces the expression of the RNA polymerase and scFv genes. The vector pMR1 carries the scFv-His6 gene under the control of the tetracycline promoter/operator ($tet^{p/o}$), and the corresponding repressor gene. The induction is carried out by adding a nontoxic analog of tetracycline, anhydrotetracycline, which is effective at a very low concentration.

b) Optimization of the Production of scFv-His6

The production of scFv-His6, estimated by the amount of scFv-His6 present in a crude periplasmic extract, is measured by indirect ELISA using an anti-His5 antibody, according to the techniques described in example 1-9. This method makes it possible to rapidly test many combinations of production parameters, such as the culture temperature, the induction time and the inducer concentration (FIG. 2).

The production of small amounts of antibody fragments from pMR1 or from pMR5, under the conditions described in example 1-6, showed that the vector pMR1 gave the best yield at 22° C., inducing for 2 hours with 0.2 μg/ml anhydrotetracycline. These same conditions were used to produce mutant scFv-His6s of mAbD1.3 (FIG. 2).

The production of large amounts of antibody fragments from pMR1 or from pMR5, under the conditions described in example 1-6, showed that the production yield was better when the induction took place during the exponential growth phase. Now, at 22° C., 2xYT medium allows only a short exponential growth phase for the HB2151 strain, between $A_{600nm}$=0.3 and $A_{600nm}$=1.1 approximately. In addition, it was observed that the bacteria became lysed in this medium. The latter was therefore supplemented with a weak base ($K_2HPO_4$) in order to avoid acidification thereof during culturing, and with compounds which stabilize the outer bacterial membrane ($MgSO_4$, glucose, NaCl). It was observed that, with the resulting medium (SB medium), the exponential growth phase was greatly extended at 22° C., up to $A_{600nm}$=3.8. This medium made it possible to obtain 4 times more scFv-His6 than in 2xYT medium, using a given culture volume.

Two types of method exist for extracting the periplasmic fluid from a bacterium: 1) the bacteria are equilibrated in a medium with a high osmotic pressure, and then transferred into a hypoosmotic buffer. The osmotic shock causes the outer membrane to rupture and the content of the periplasm is recovered in the second buffer; 2) the bacteria are resuspended in an outer membrane-lysing buffer (EDTA, amphiphilic peptides such as polymyxin B). The content of the periplasm is then recovered in a single step. Four methods for preparing the periplasmic extract from HB2151(pMR1), described in example 1-7, were tested, and the amount of scFv-His6 present in each extract was estimated by ELISA. The product of the measurements of $A_{405nm}$ by the volume of the extract gave the following relative values: 100±6 for the osmotic shock method (mean ± standard error over 3 measurements), 58±9 for the Tris-EDTA method, 61±8 for the Tris-EDTA-NaCl method and 106±9 for the polymyxin B method. The latter method gave the best results and was therefore used for the productions of wild-type and mutant scFv-His6s in large volume.

3-Purification of scFv-His6

The polyhistidine tail of the scFv-His6s allows them to be purified on a Ni-NTA immobilized nickel column, according to the protocol described in example 1-8. After the column has been loaded with the periplasmic extract, washing and elution are carried out with various concentrations of imidazole, which competes with the histidines for the nickel coordination. The imidazole concentration for the washing, which makes it possible to detach the impurities without displacing the scFv-His6 itself, and the concentration for the elution, which makes it possible to detach the scFv-His6 in a minimal amount of fractions without denaturing it, are specified in example 1-8. The purity of the elution fractions was analyzed by SDS-polyacrylamide gel electrophoresis and Coomassie blue staining, according to the protocol described in example 1-10. These fractions contain a protein which has an apparent molecular mass equal to the expected mass for the scFv-His6s, and are 95% pure. The losses of material due to the nonbinding to the nickel or to the detachment during the washes were estimated. The product of the measurements of $A_{405nm}$ by the volume of each fraction gave the following relative values: of the 100% contained in the crude extract, 6.7% of the scFv-His6s do not bind to the column, 7.6% are detached during the washes and 85.6% are in the elution fractions. Under the optimal conditions for culturing, extraction and purification, 650 μg of purified wild-type scFv-His6 were obtained per liter of culture.

Figure 4:
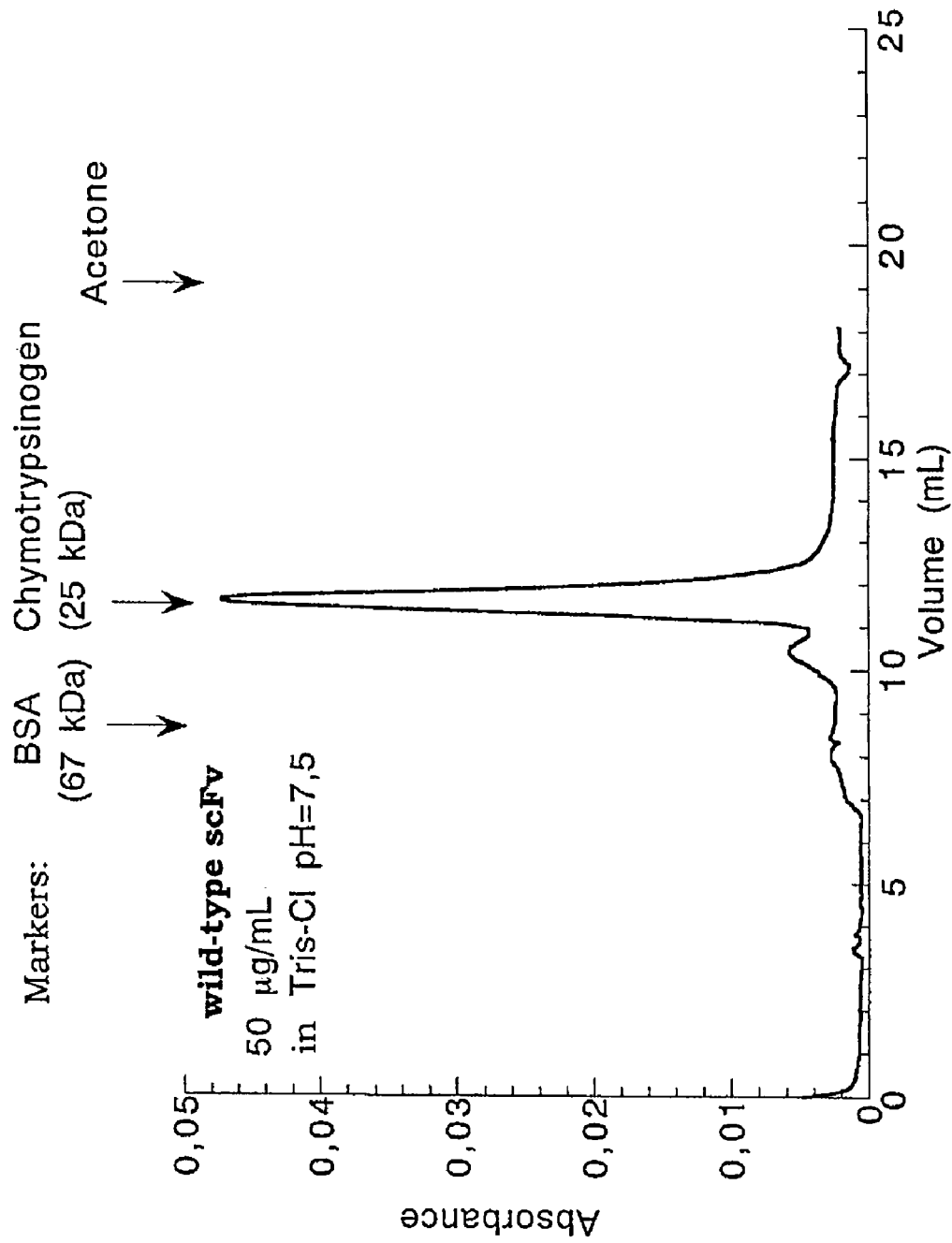

4-Properties of Oligomerization and of Binding to Lysozyme of the Wild-Type scFv-His6 (FIG. 4)

The BIAcore apparatus makes it possible to rapidly obtain the rate constants for association $k_{on}$ and dissociation $k_{off}$ between antibody and antigen, and also the equilibrium constant $K'_D = k_{off}/k_{on}$, at the interface between the buffer and the surface on which the antigen has been immobilized. Since the measurements are taken under continuous flow over the surface, they may be distorted by the recapturing of recently dissociated svFvs on another immobilized antigen site. This recapturing has little influence with a monovalent antibody fragment, and it is limited by adding antigen in solution in the dissociation buffer. However, the scFvs are capable of forming dimers by association of the VH domain of one molecule with the VL domain of another (Arndt et al., 1998). These dimers have two antigen-binding sites. They lead to an increased probability of recapture.

Figure 2:
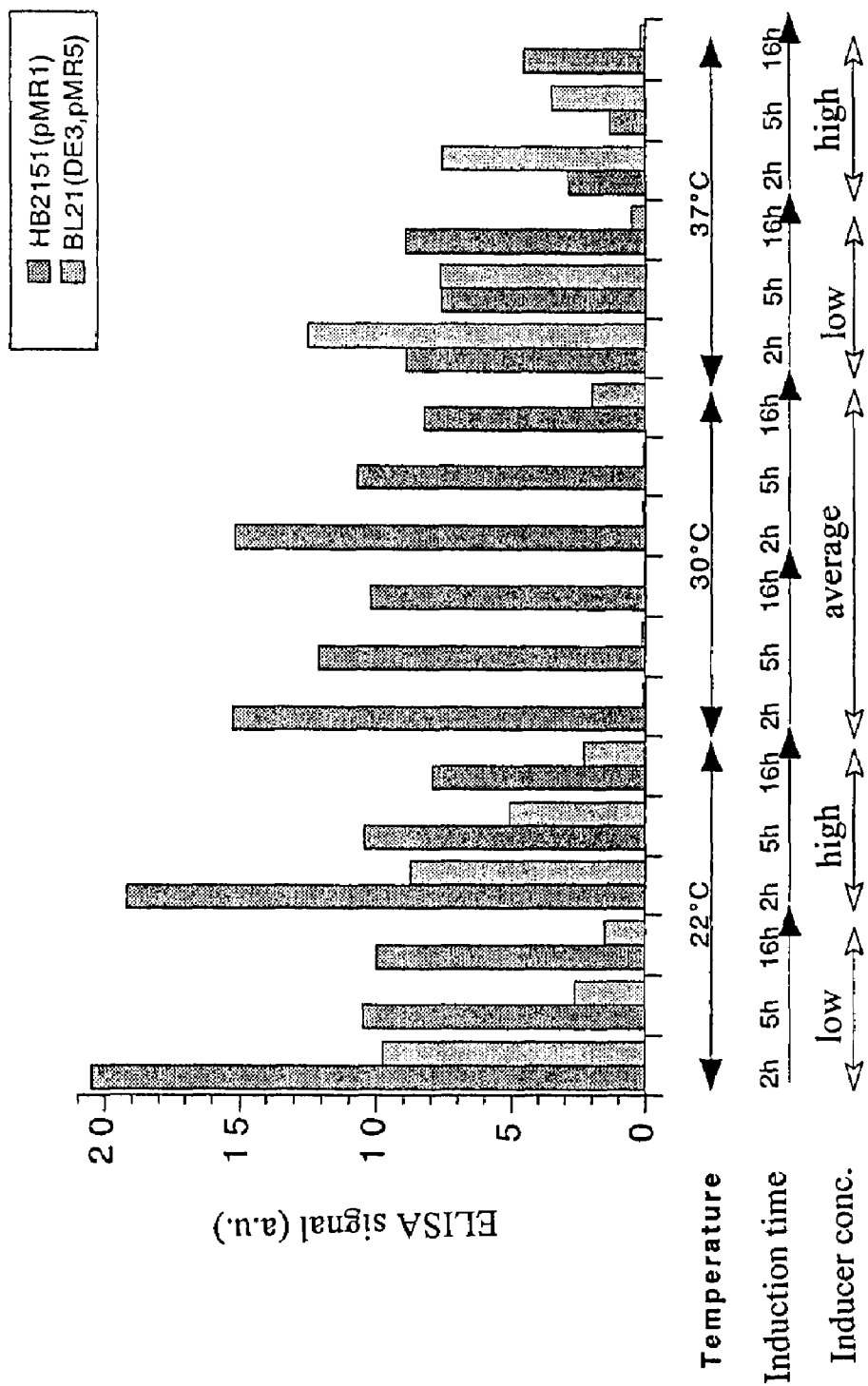
Figure 3:
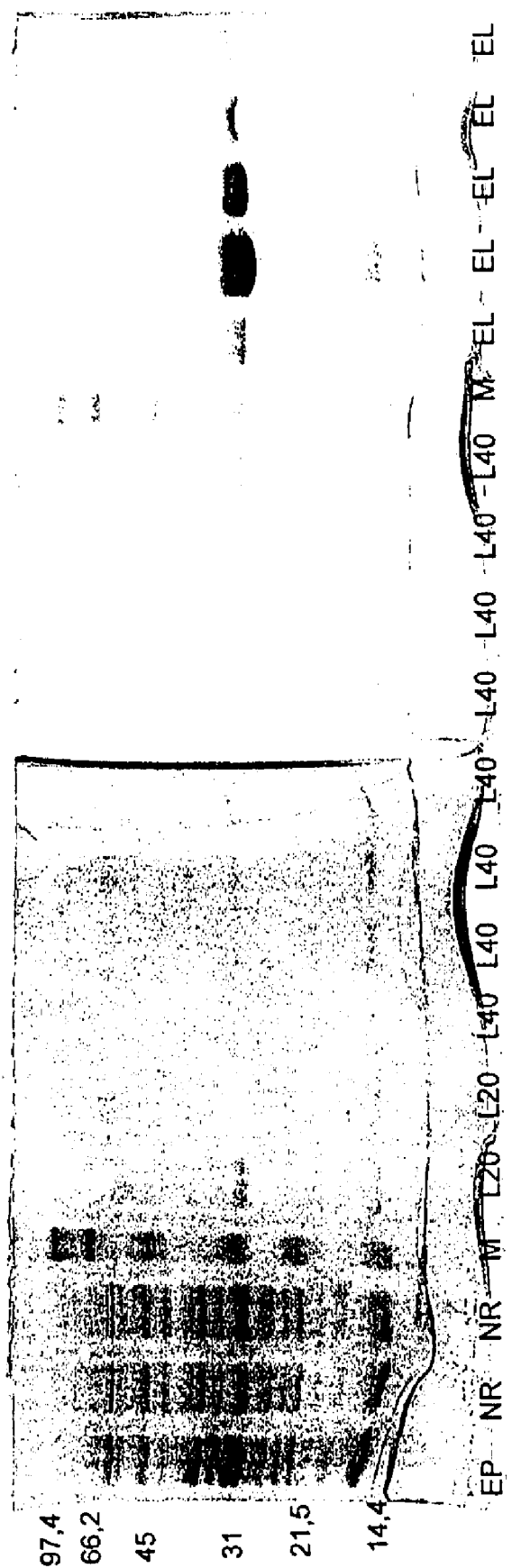

Before carrying out the measurements on BIACORE™, it is therefore necessary to verify the dimerization state of the scFv-His6 of mAbD1.3. The proportions of monomer and of dimmer at the pH used for the BIACORE™ (pH 7.5) and at a concentration of 50 μg/ml were estimated by the height of the corresponding peaks in exclusion chromatography, according to the protocol of example 1-12, and the results are given in FIG. 4. The ratio of the dimmer peak surface area to the monomer peak surface area gives a degree of dimerization of 9.8%. This low degree makes it possible to disregard the effect of recapturing on the surface during the measurements on BIACORE™. In addition, these measurements were made at concentrations of 0.1 to 20 μg/ml, less than the 50 μg/ml used for the exclusion chromatography. The kinetic parameters for the interaction between the scFv-His6 and the lysozyme, determined on BIACORE™, according to the protocol described in example 1-11, as follows:

$k_{on}$=1.15(±0.15)0.10$^5$M$^{-1}$.s$^{-1}$ $k_{off}$=1.20(±0.22)0.10$^{-3}$s$^{-1}$ $K'_D$=10.5 (±3.3) nM 5-Construction, Production and Purification of Mutant scFv-His6s (FIG. 3)

The mutations to cysteine of the residues of the antibody mAbD1.3, placed in the first class (VH-T30C, VL-T53C, VL-S93C and VL-T94C, see also paragraph 1 of this example and column 10 of FIG. 1) were introduced into the expression vector pMR1 using the Kunkel method described in example 1-4. The oligonucleotides used, described in example 1-3, were designed to introduce or delete restriction sites. The mutation can then be detected by analysis of the fragments obtained after cleavage. The mutant clones were also sequenced in the region of the mutation, using the oligonucleotides described in example 1-3, according to the method described in example 1-4, in order to verify the integrity of the sequence. The plasmid derived from pMR1 carrying the mutation VL-S93C, named pMR1(VL-S93C), corresponds to SEQ ID NO:11. The ability of several mutant derivatives of pMR1 to express the scFv-His6 was tested under the conditions described for the production of the wild-type scFv-His6 from pMR1 (example 2-2). The results show that these mutants are produced efficiently in comparison with the wild-type: 100±12 for the wild-type, 100±29 for VL-S93C, 97±5 for VL-T94C. The VL-S93C mutant was purified with yields of 575 μg per liter of culture, comparable to those obtained with the wild-type scFv-His6.

The purity of the elution fractions was analyzed by SDS-polyacrylamide gel electrophoresis and COOMASIE® blue staining, according to the protocol described in example 1-10. The results obtained are given in FIG. 3. These fractions contain a protein which has an apparent molecular mass equal to the mass expected for the scFv-His6s, and are 95% pure.

Figure 5:
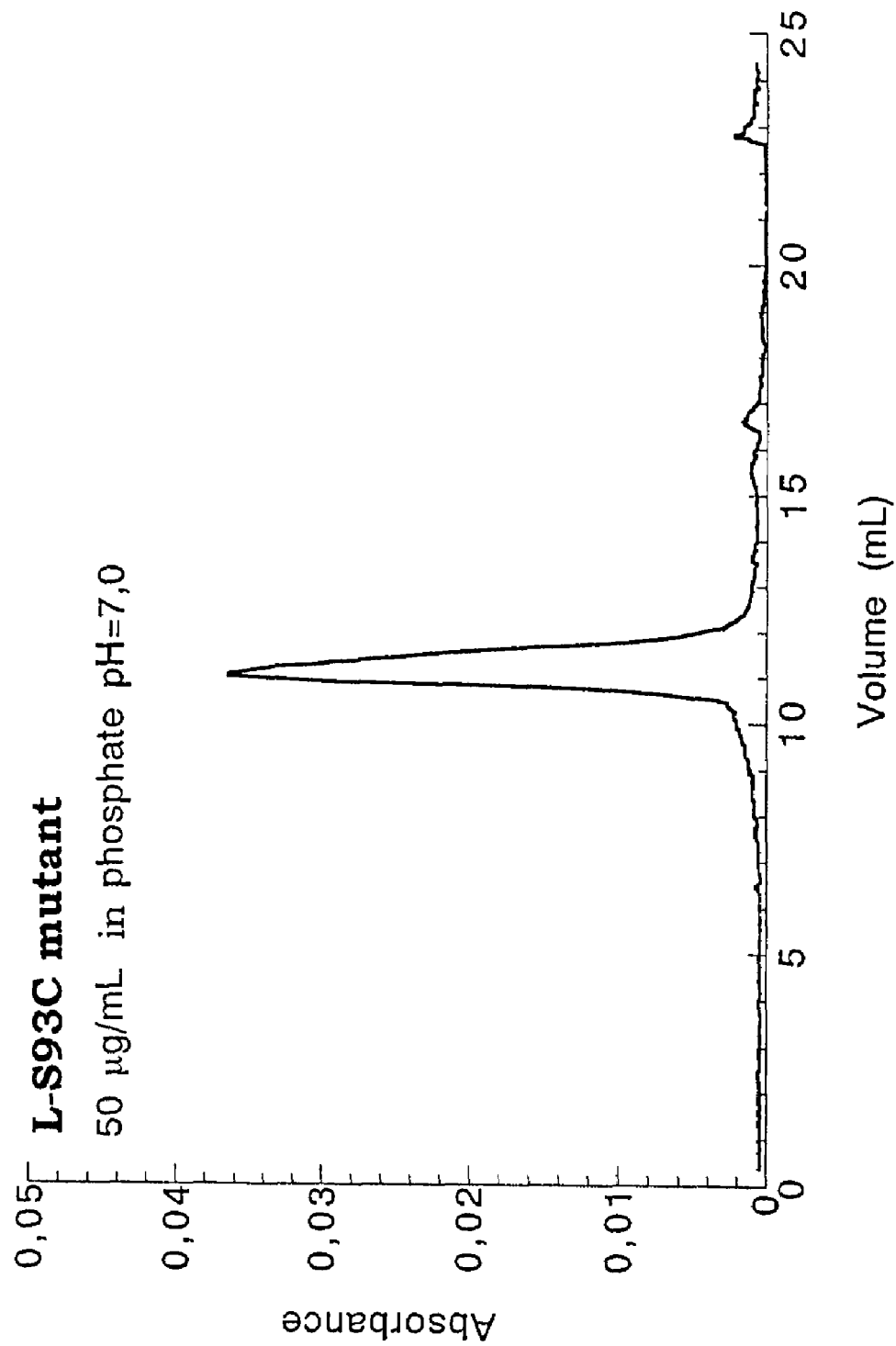
Figure 6:
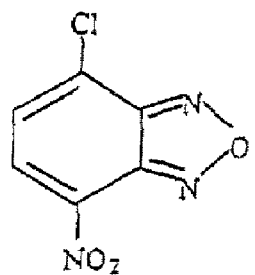
FIG. 6 represents the chemical structures of CNBD, of IANBD, of 5-iodoacetamidofluorescein (5-IAF) and of acrylodan.
Figure 6:
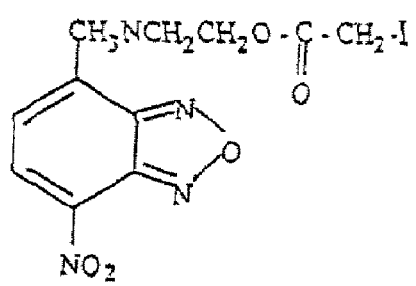
Figure 6:
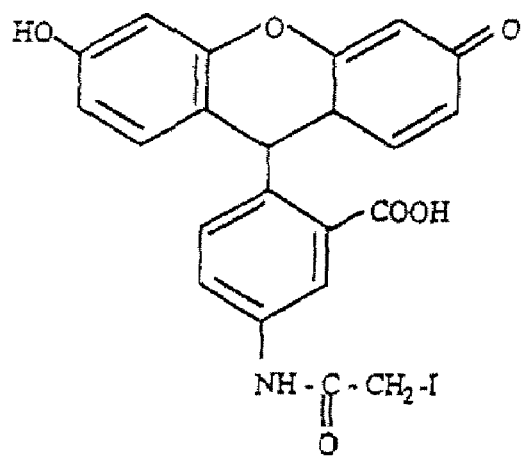
Figure 6:
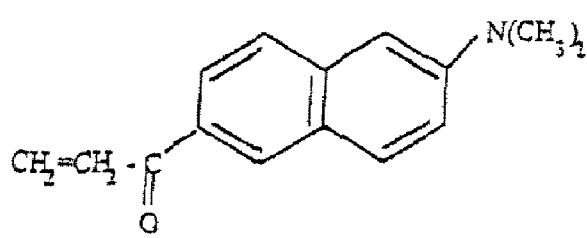

6-Absence of Covalent Dimerization of the VL-S93C Mutant (FIG. 5)

The presence of a free cysteine on the mutant scFv-His6s may lead to the formation of interference intermolecular disulfide bridges during production or purification or during coupling of the fluorophore. The scFv-His6(VL-S93C), dialyzed against the coupling buffer, was analyzed by exclusion chromatography under the conditions used for the wild-type scFv-His6 (example 1-12 and example 2-4). The chromatogram shows only one peak, suggesting that the scFv-His6 (VL-S93C) exists in only a single state of oligomerization in the buffer used (FIG. 5). The position of this peak corresponds virtually to that of the monomeric wild-type scFv-His6. The small difference between the positions of these two peaks may be due to the fact that the two chromatograms were developed in buffers which were different in nature and had slightly different pHs.

7-Coupling of Fluorophores to the VL-S93C Mutant (FIGS. 6 to 10)

Figure 7:
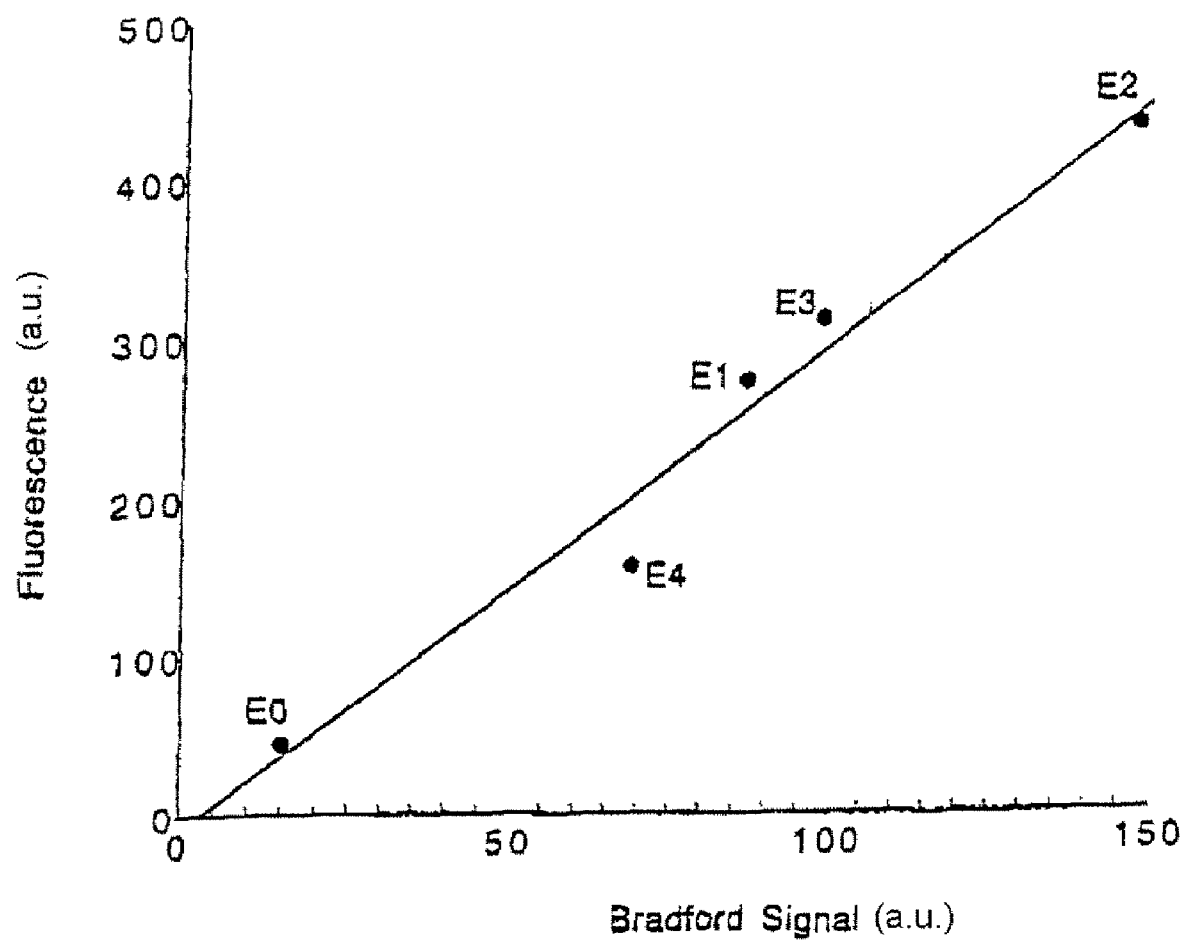
FIG. 7 illustrates the proportionality between fluorescence intensity (excitation at 469 nm, emission at 535 nm) and protein concentration in the elution fractions derived from the separation between conjugate and free fluorophore.

The coupling of IANBD (FIG. 6) to scFv-His6(VL-S93C) is carried out after treating the antibody fragment with various concentrations of 2-mercaptoethanol and desalting, according to the protocol described in example 1-13. The reaction is carried out at pH=7.0 in order to avoid interference coupling on lysines deprotonated at basic pH (Houk et al., 1983; Del Boccio et al., 1991). After coupling, the excess fluorophore and the scFv-His6(VL-S93C) derivative are separated by further purification on a nickel column. Several arguments converge to confirm the specificity of the coupling on the cysteine VL-Cys93 of the mutant scFv. During the repurification, the fluorophore is effectively washed and the residual fluorescence is eluted from the column at the same time as the scFv. In the elution fractions, the fluorescence intensity is proportional to the amount of protein, which suggests stoichiometric coupling (FIG. 7).

Figure 8:
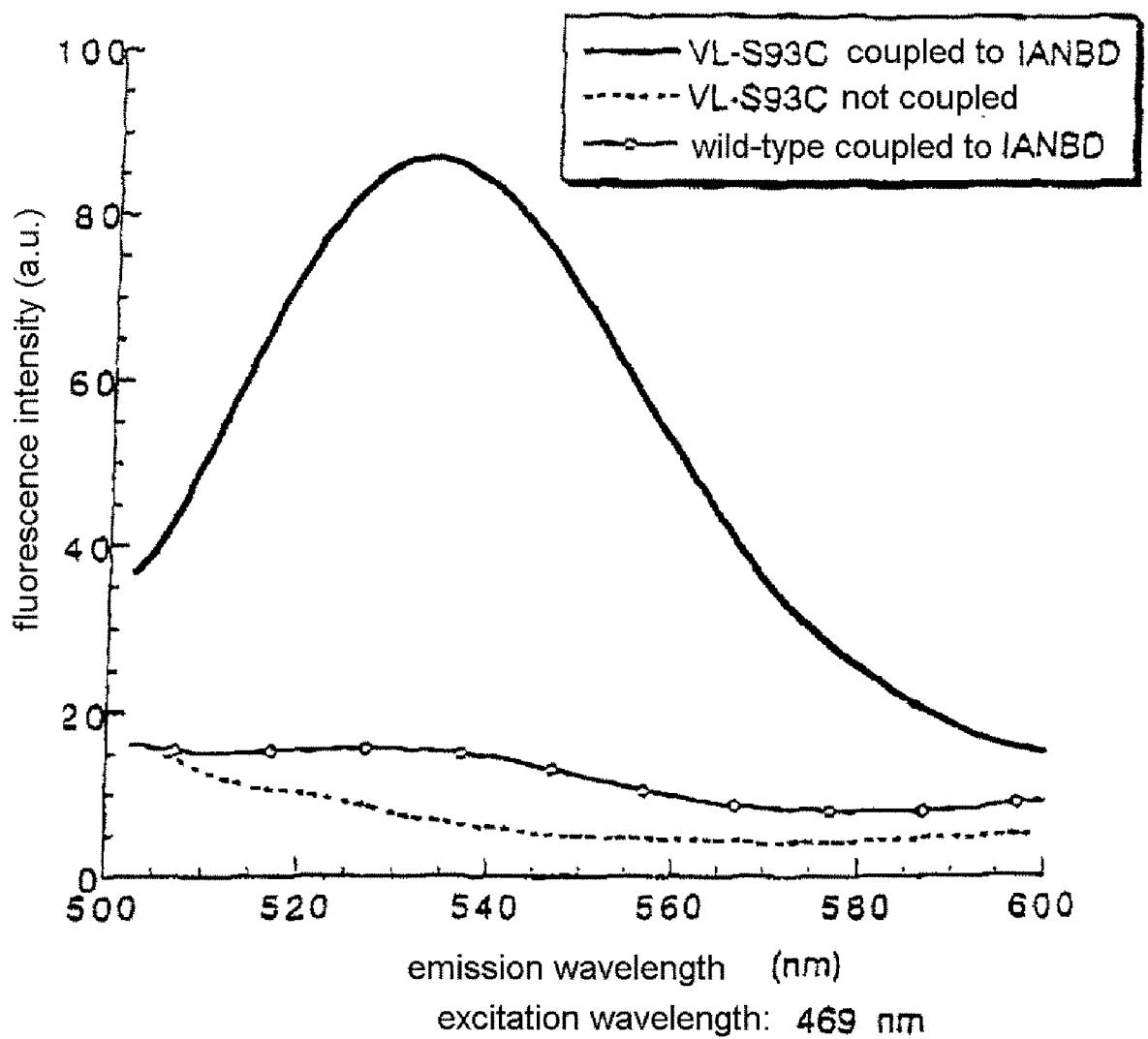
FIG. 8 illustrates the fluorescence emission by scFv-His6 derivatives, for an excitation at 469 nm, in the absence of lysozyme. The following species were analyzed: wild-type scFv-His6 and scFv-His6(VL-S93C) after coupling with IANBD and separations; sFv-His6 (VL-S93C) before coupling.
Figure 10:
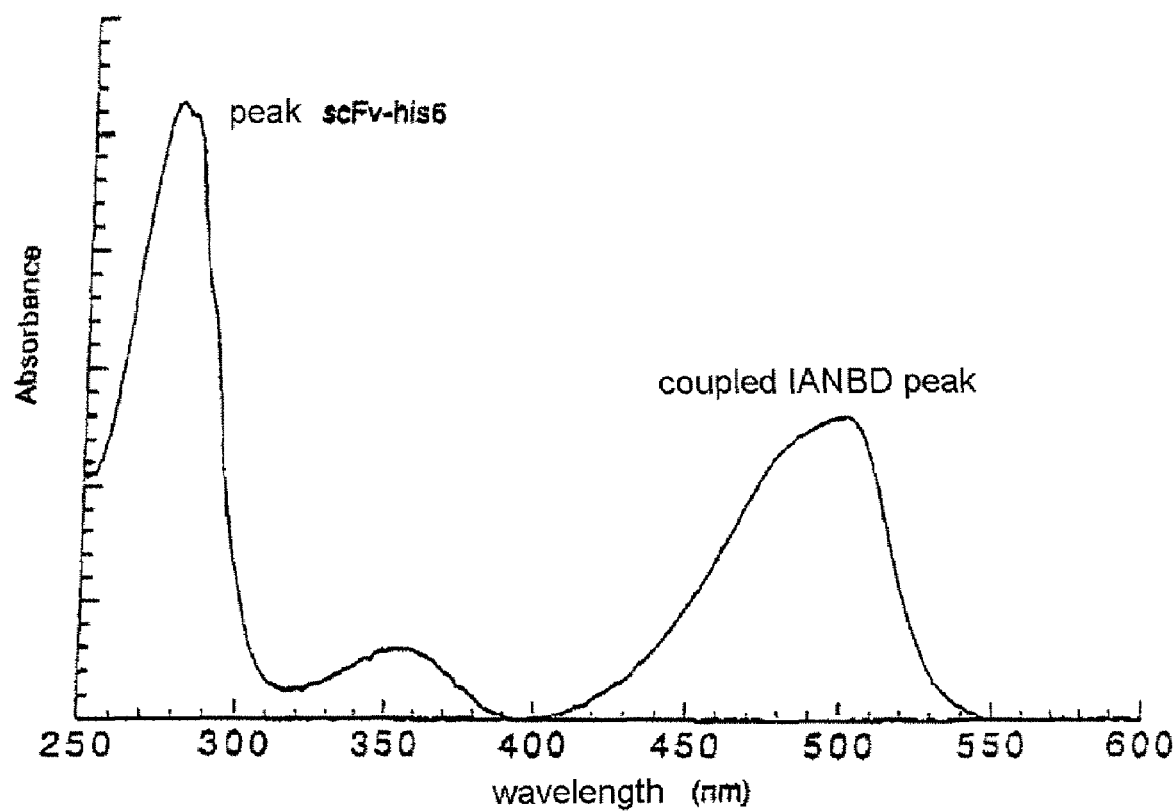
FIG. 10 shows the absorption spectrum of the fluorescent derivative scFv-His6(V-S93ANBD), recorded for wavelengths of 250 to 550 nm. The height of the peak at 278 nm, corresponding to the protein, and that of the peak at 500 nm, corresponding to the coupled IANBD, made it possible to calculate the coupling yield (here 83%).

In the absence of reducing treatment, the wild-type scFv-His6 shows virtually no reaction with IANBD, whereas the scFv-His6(VL-S93C) shows a degree of labeling with the fluorophore of 8% (FIG. 8). The latter yield is greatly improved when the scFv-His6(VL-S93C) is reduced with 2-mercaptoethanol, rapidly desalted and placed in the presence of IANBD. On the other hand, this treatment causes a loss of material which increases the more thorough the reduction. It is probable that the scFv-His6 is made partly insoluble by the reduction of its disulfide bridges. The loss of material during the desalting (−30%) and repurification (−15%) steps also intervenes in the overall coupling yield. A concentration of 10 mM of 2-mercaptoethanol made it possible to obtain satisfactory coupling yields with two different mutants (FIGS. 9 and 10), while at the same time preserving sufficient material for the fluorescence measurements.

8-Variations in the Fluorescence of the VL-S93C Mutant Coupled to a Fluorophore, as a Function of the Antigen Concentration (FIG. 11 and FIG. 12)

A spectrum of emission from the scFv-His6(VL-S93ANBD) conjugate, taken immediately after the addition of antigen (lysozyme), shows an enhancement of the fluorescence which depends on the final concentration of antigen. The fluorescence intensity saturates at 1.26±0.05 times that of the free biosensor when the antigen concentration is sufficient, and reproducibly over several preparations of biosensors. No significant shift in the wavelength of the emission maximum is observed (FIG. 11).

The fluorescence intensities were recorded in the absence or in the presence of varying concentrations of lysozyme (10 nM to 2 µM) in a 50 mM Tris-HCl, 150 mM NaCl buffer, pH 7.5.

The results given in FIG. 12 show that, in this buffer, the fluorescence intensity of the scFv-His6 (VL-S93ANBD) conjugate is proportional to the concentration of lysozyme up to 400 nM and increased by 91% at saturation. The curve obtained makes it possible to directly titrate the lysozyme between 10 and 400 nM.

Consequently, the results obtained in FIG. 12 illustrate that the biosensor according to the invention advantageously makes it possible to directly titrate an antigen or a hapten, for example in a body fluid.

9-Coupling Yield and Variation in Fluorescence, as a Function of the Antigen Concentration, of a Series of scFv-His6 Mutants (FIG. 13)

ScFv-His6 mutants, selected according to the method described in example 2-1, were produced in a similar way to the VL-S93C mutant (example 2-5), according to the methods described in example 1 (1-1 to 1-12). Thus, plasmids derived from pMR1 (SEQ ID NO:10) carrying the mutations described in FIG. 12 were constructed by site-directed mutagenesis using the oligonucleotides given in table II. The scFv-His6 mutants produced from these plasmids were coupled to IANBD, in a similar way to the VL-S93C mutant (example 2-7), using a mercaptoethanol concentration of 10 mM, according to the protocol described in example 1-13. The results given in FIG. 13 show that satisfactory coupling yields are obtained for virtually all the coupling positions selected, and that considerable enhancements of fluorescence are observed for more than half these coupling positions.

REFERENCES

Arndt K. M. et al., Biochemistry, 1998, 37, 12918-12926.
Bhat T. N. et al., Proc. Natl. Acad. Sci. USA, 1994, 91, 1089-1096.
Braden B. C. et al., Immunological Review, 1998, 163, 45-57.
Carter P. et al., Nucleic Acids Research, 1985, 13, 4431-4443.
Creighton T. E., Proteins: Structure and molecular properties (Second edition). W. H. Freeman and Cie, 1996, 227-229.
Dall'Acqua W. et al., Biochemistry, 1996, 35, 9667-9676.
Dall'Acqua. W. et al., Current Opinion in Structural Biology, 1998, 8, 443-450.
Del Boccio G. et al., The Journal of Biochemical Chemistry, 1991, 266, 13777-13782.
England P. et al., Biochemistry, 1997, 36, 164-172.
England P. et al., The Journal of Immunology, 1999, 162, 2129-2136.
Gilardi G. et al., Analytical Chem., 1994, 66, 3840-3847.
Glockshuber R. et al., Biochemistry, 1992, 31, 1270-1279.
Goldbaum F A. et al., J. Mol. Recogn., 1996, 9, 6-12.
Haugland R. P., Handbook of fluorescent probes and research chemicals (sixth edition). Molecular Probes Inc., Eugene Oreg., 1996.
Hawkins R E. et al., J. Mol. Biol., 1993, 234, 958-964.
Houk W. T. et al., The Journal of Biological Chemistry, 1983, 258, 9:5419-5423.
Ito W. et al., J. Biol. Chem., 1993, 268, 16639-16647.
Ito W. et al., J. Mol. Biol., 1995, 248, 729-732.
Kunkel T. A. et al., Methods in Enzymology, 1987, 154, 367-382.
Langedijk A. C. et al., Journal of Molecular Biology, 1998, 283, 95-110.
Marvin J. S. et al., Proc. Natl. Acad. Sci. USA., 1997, 94, 4366-4371.
Marvin J. S. et al., J. Am. Chem. Soc., 1998, 120, 7-11.
Pace C. N. et al., Protein Structure, 1995, 4, 2411-2423.
Piervincenzi R T. et al., Biosensors & Bioelectronics, 1993, 13, 305-312.
Pollack S. J. et al., Science, 1988, 242, 1038-1040.
Plückthun A. et al., Antibody engineering, a practical approach. McCaffert, J., Hoogenboom, H. R. and Chiswell, D. J. Eds. Oxford University Press, 1996, 203-252.

Rees A. R. et al., Protein structure prediction, a practical approach. *Sternberg M. J. E. Ed. Oxford University Press*, 1996, 141-172.
Saleemuddin M., *Adv. Biochem. Eng. Biotech.*, 1999, 64, 203-226.
Sambrook J. et al., Molecular cloning: a laboratory manual. *Cold Spring Harbor Laboratory Press*, 1989.
Sara M. et al., *Micron.*, 1996, 27, 141-156.
Skerra, A., *Gene*, 1994, 51, 131-135.
Sloan D. J. et al., *Protein Engineering*, 1998, 11, 819-23.
Sternberg M. J. E., Protein Structure Prediction, a practical approach. *Oxford University Press*, 1996.
Studier F. W. and Moffatt, B. A., *Journal of Molecular Biology*, 1986, 189, 113-130.
Tolosa L. et al., *Analytical Biochem.*, 1999, 267, 114-120.
Turkova J., *J. Chromatography*, 1999, 722, 11-31.
Vriends G., *Journal of Molecular Graphism*, 1990, 8, 52-56.
Weetall H. H. *Appl. Biochem. Biotech.*, 1993, 41, 157-188.
Yoshioka M. et al., *J. Chromatography*, 1991, 566, 361-368.
Ysern X. et al., *J. Mol. Biol.*, 1994, 238, 496-500.

As emerges from the above, the invention is in no way limited to its methods of implementation, preparation and application which have just been described more explicitly; on the contrary, it encompasses all the variants thereof which may occur to a person skilled in the art, without departing from the context or the scope of the present invention.

The invention claimed is:

1. A method for preparing a biosensor consisting of (i) at least one fragment of a receptor which is a protein having one or more disulfide bridges, wherein said receptor fragment is capable of binding to a suitable ligand via an active site to form a receptor fragment-ligand complex, and in which receptor fragment at least one of its amino acid residues located in the proximity of said active site is naturally present in the form of a Cys residue, or is substituted with a Cys residue, and (ii) a fluorophore coupled to said Cys residue(s), comprising:

(a) selecting residues of the receptor by searching for the residues which, in the receptor-ligand complex, (i) are in direct contact with the ligand, or (ii) are in contact via a water molecule, or (iii) have a solvent accessible surface area (ASA) which is modified by the binding of the ligand, when use is made of spheres of increasing radius of 1.4 to 30 Å, preferably of 1.4 to 2.9 Å, for the molecule of said solvent;

(b) calculating the solvent accessible surface area (ASA), for the free receptor, of the atoms in the γ position and, optionally, in the δ position for each residue selected in (a), using a sphere of 1.4 Å, and selecting the residues in which the atom in the γ position or the atom in the δ position is accessible to the solvent;

(c) mutating by site-directed mutagenesis at least one of the residues selected in (b) to a Cys residue when said residue is not naturally a Cys residue, and (d) coupling the Sγ atom of at least one Cys residue obtained in (b) or in (c) to a fluorophore.

2. The method of claim 1, wherein, in step (b), the ASA values for a residue Xi in the i position of the sequence of the receptor are expressed in the form of percentages of the corresponding ASA values in a tripeptide Gly-$X_i$-Gly, which would adopt the same configuration as the tripeptide $X_{i-1}$-$X_i$-$X_{i+1}$ in the structure of the receptor.

3. The method of claim 1, wherein, prior to step (a), it comprises a step of modeling the receptor and/or the ligand and/or the receptor-ligand complex.

4. The method of claim 1, wherein, prior to step (a), the nonessential Cys residues of the receptor are substituted with Ser or Ala residues by site-directed mutagenesis.

5. The method of claim 1, wherein, in step (d), said fluorophore is selected from the group consisting of IANBD, CNBD, acrylodan, 5-iodoacetamidofluorescein or a fluorophore having an aliphatic chain of 1 to 6 carbon atoms.

6. The method of claim 1, wherein, in step ($d_1$), said fluorophore is selected from the group consisting of IANBD, CNBD, acrylodan, 5-iodoacetamidofluorescein or a fluorophore having an aliphatic chain of 1 to 6 carbon atoms.

7. The method of claim 1, wherein, prior to step (d), the mutated receptor obtained in step (c) is subjected to a controlled reduction.

8. The method of claim 1, wherein, after step (d), it comprises an additional step (e) for purifying the biosensor.

9. The method of claim 8, wherein, after step (e), it comprises an additional step for measuring the equilibrium constant ($K_D$ or $K'_D$) for said purified biosensor, or the dissociation ($K_{off}$) and association ($k_{on}$) rate constants for the receptor and ligand.

10. The method of claim 1, wherein, after step (d) or (e), it comprises an additional step for immobilizing the biosensor on a solid support.

11. A method for preparing a biosensor consisting of (i) at least one fragment of a receptor which is a protein having one or more disulfide bridges, wherein said receptor fragment is capable of binding to a suitable ligand via an active site to form a receptor fragment-ligand complex, and in which receptor fragment at least one of its amino acid residues located in the proximity of said active site is naturally present in the form of a Cys residue, or is substituted with a Cys residue, and (ii) a fluorophore coupled to said Cys residue(s), comprising:

(a$_1$) identifying the active site of the receptor by mutagenesis of the set, or of a subset, of the residues of the receptor, and determining the variations in the parameters of interaction with the ligand ($K_D$, $k_{on}$, $k_{off}$) which are due to each mutation or to limited groups of mutations;

(b$_1$) selecting the Cys residues, or the residues to be mutated to cysteine, from the residues of the receptor which are located in the proximity of the residues of the active site along the sequence;

(c$_1$) mutating by site-directed mutagenesis at least one of the residues selected in (b$_1$) to a Cys residue when said residue is not naturally a Cys residue; and (d$_1$) coupling the Sγ atom of at least one Cys residue obtained in (b$_1$) or in (c$_1$) to a fluorophore.

12. The method of claim 11, wherein, prior to step (a$_1$), the nonessential Cys residues of the receptor are substituted with Ser or Ala residues by site-directed mutagenesis.

13. The method of claim 11, wherein, prior to step (d$_1$), the mutated receptor obtained in step (c$_1$) is subjected to a controlled reduction.

14. The method of claim 11, wherein, after step (d$_1$), it comprises an additional step (e$_1$) for purifying the biosensor.

15. The method of claim 14, wherein, after step (e$_1$), it comprises an additional step for measuring the equilibrium constant ($K_D$ or $K'_D$) for said purified biosensor, or the dissociation ($K_{off}$) and association ($k_{on}$) rate constants for the receptor and ligand.

16. The method of claim 11, wherein, after step (d$_1$) or (e$_1$), it comprises an additional step for immobilizing the biosensor on a solid support.

* * * * *